US012702508B1

(12) United States Patent
Crozier et al.

(10) Patent No.: US 12,702,508 B1
(45) Date of Patent: Aug. 11, 2026

(54) SYSTEMS, DEVICES, AND METHODS FOR SEALING AND VENTING A SURGICAL INSTRUMENT OF A SURGICAL ROBOTIC SYSTEM

(71) Applicant: Distalmotion SA, Epalinges (CH)

(72) Inventors: James Crozier, Cully (CH); Benoit Della Rosa, Epalinges (CH)

(73) Assignee: Distalmotion SA, Epalinges (CH)

( * ) Notice: Subject to any disclaimer, the term of this patent is extended or adjusted under 35 U.S.C. 154(b) by 0 days.

(21) Appl. No.: 19/286,070

(22) Filed: Jul. 30, 2025

(51) Int. Cl.
*A61B 34/35* (2016.01)
*A61B 34/00* (2016.01)
*A61B 34/30* (2016.01)

(52) U.S. Cl.
CPC .............. *A61B 34/35* (2016.02); *A61B 34/76* (2016.02); *A61B 2034/302* (2016.02)

(58) Field of Classification Search
CPC ... A61B 34/35; A61B 34/76; A61B 2034/302; A61B 34/70; A61B 34/71
USPC .......... 606/1, 130, 169, 170, 219; 227/175.1
See application file for complete search history.

(56) References Cited

U.S. PATENT DOCUMENTS 8,939,963 B2 1/2015 Rogers et al.
10,413,374 B2 9/2019 Chassot et al.
10,646,294 B2 5/2020 Beira
10,806,538 B2 * 10/2020 Farritor ................ A61B 90/361
11,058,503 B2 7/2021 Chassot et al.
12,295,688 B2 5/2025 Chassot et al.
2009/0216248 A1 8/2009 Uenohara et al.
2014/0005661 A1 * 1/2014 Shelton, IV ....... A61B 18/1445 606/41
2019/0274781 A1 * 9/2019 Lambrecht ............. A61B 34/30
2021/0315660 A1 * 10/2021 Williams ......... A61B 17/00234
(Continued)

FOREIGN PATENT DOCUMENTS

WO WO-2015175200 A1 11/2015
WO WO-2016183054 A1 11/2016
(Continued)

OTHER PUBLICATIONS

U.S. Appl. No. 19/431,629, filed Dec. 23, 2025; Inventor Rozand, Guillaume et al.
(Continued)

*Primary Examiner* — Carl H Layno
*Assistant Examiner* — Mary Grace Schlueter
(74) *Attorney, Agent, or Firm* — Cooley LLP

(57) ABSTRACT

Devices, systems, and methods herein relate to surgical robotic systems, for example, a surgical instrument removably coupled to a robotic arm. Devices may include a shaft including a proximal end and a distal end. The shaft may define a lumen extending between the proximal end and the distal end. An end effector may be disposed at the distal end of the shaft. A proximal head may be disposed at the proximal end of the shaft. The proximal head may include a housing defining an internal space configured to house a plurality of engagement elements and a knob body disposed proximal of the housing. Each engagement element may be coupled to the end effector via a force transmitting element disposed within the lumen. The knob body may be configured to be distally translated and subsequently rotated relative to the housing to lock the proximal head to an instrument interface.

28 Claims, 30 Drawing Sheets

(56) References Cited

U.S. PATENT DOCUMENTS

| | | | | |
|---|---|---|---|---|
| 2022/0079696 | A1* | 3/2022 | Nichols .................... | A61B 1/04 |
| 2022/0080602 | A1* | 3/2022 | Nobles ................... | A47C 7/543 |
| 2024/0006048 | A1* | 1/2024 | Shelton, IV ... | A61B 17/320092 |

FOREIGN PATENT DOCUMENTS

| | | | |
|---|---|---|---|
| WO | WO-2017015599 | A1 | 1/2017 |
| WO | WO-2018207136 | A1 | 11/2018 |
| WO | WO-2019155383 | A1 | 8/2019 |
| WO | WO-2020141487 | A2 | 7/2020 |
| WO | WO-2024084422 | A1 | 4/2024 |

OTHER PUBLICATIONS

U.S. Appl. No. 19/346,327, filed Sep. 30, 2025, Inventor Nicolet, Romain et al.

U.S. Appl. No. 19/346,365, filed Sep. 30, 2025, Inventor Rosa, Benoit Della et al.

U.S. Appl. No. 19/402,449, filed Nov. 26, 2025; Inventor Crozier, James.

* cited by examiner

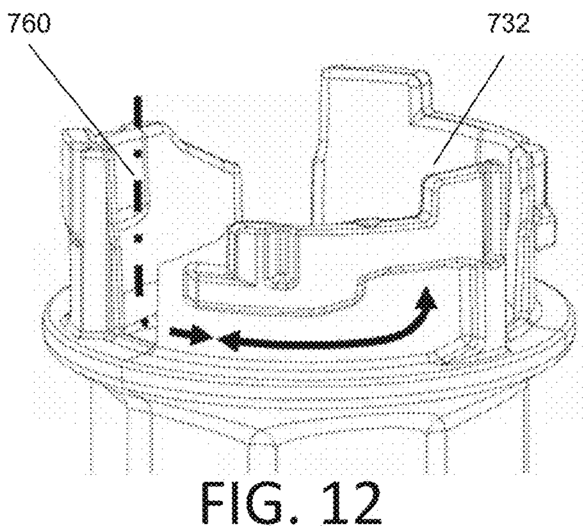
FIG. 12
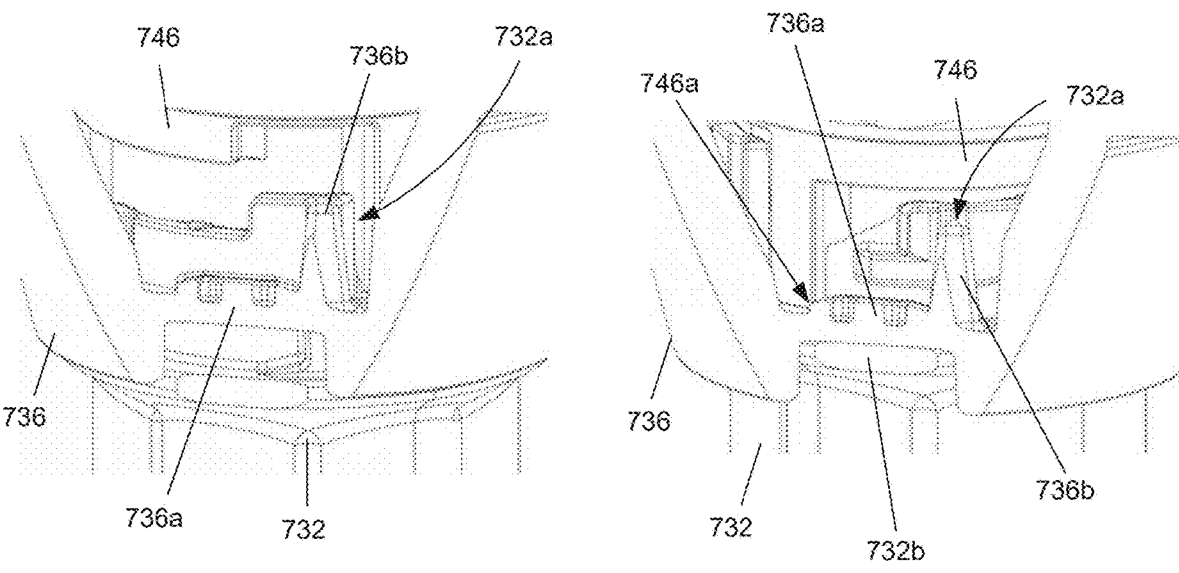
FIG. 13A
FIG. 13B

SYSTEMS, DEVICES, AND METHODS FOR SEALING AND VENTING A SURGICAL INSTRUMENT OF A SURGICAL ROBOTIC SYSTEM

TECHNICAL FIELD

The devices, systems, and methods herein relate to surgical robotic systems, for example, a surgical instrument removably couplable to a robotic arm.

BACKGROUND

Traditional surgical robotic systems may include a robot such as a robotic arm coupled to a surgical instrument through a sterile interface. The robotic arm may include a hub configured to drive the surgical instrument. The sterile interface facilitates the transmission of force and movements from the hub to the surgical instrument. Accordingly, a robust connection should be formed when the surgical instrument is coupled to the robot. Some conventional systems may include male features on a knob of the surgical instrument and corresponding female features on the sterile interface for coupling. For example, the surgical instrument may be inserted into a lumen of the sterile interface, and the knob may be rotated (e.g., turned) to mechanically couple the instrument to the sterile interface using the male and female features. However, some users may find the process of uncoupling the surgical instrument from the sterile interface to be unintuitive. Moreover, some surgical instruments have open channels that may be useful for gas sterilization, but may increase the risk of fluid contamination of the sterile interface and hub. As such, additional devices, systems, and methods for a surgical instrument are desirable.

SUMMARY

Devices, systems, and methods herein relate to a surgical instrument having a coupling mechanism providing improved ergonomics, liquid management, and sterilization. In some embodiments, an apparatus may comprise a shaft including a proximal end and a distal end. The shaft may define a lumen extending between the proximal end and the distal end. An end effector may be disposed at the distal end of the shaft. A proximal head may be disposed at the proximal end of the shaft. The proximal head may include a housing defining an internal space configured to house a plurality of engagement elements and a knob body disposed proximal of the housing. Each engagement element of the plurality of engagement elements may be coupled to the end effector via a force transmitting element disposed within the lumen. The knob body may be configured to be distally translated and subsequently rotated relative to the housing to lock the proximal head to an instrument interface of a surgical robotic system such that the plurality of engagement elements can be coupled to one or more actuators configured to drive movement of the plurality of engagement elements to move the end effector in at least one degree-of-freedom.

In some embodiments, the knob body may include one or more arms configured to interface with one of more corresponding features disposed on the housing to provide audible and/or haptic feedback to a user when the knob body is distally translated and subsequently rotated relative to the housing. In some embodiments, a spring may be disposed within the internal space of the housing. The knob body may be configured to distally translate relative to the housing in response to a force being applied to the knob body that is sufficient to compress the spring.

In some embodiments, a first manifold structure may define one or more ports. A second manifold structure may define one or more channels. The first manifold structure may be configured to rotate between a first position and a second position relative to the second manifold structure. When the first manifold structure is in the first position, the one or more ports and the one or more channels may be aligned and configured to allow passage of a cleaning fluid into the interior space and other interior regions of the apparatus to facilitate cleaning and/or sterilization of internal components of the apparatus. When the first manifold structure is in the second position, the one or more ports and the one or more channels may be misaligned with each other and configured to seal the interior space and other interior regions of the apparatus to prevent fluids from leaving the interior space and other interior regions.

In some embodiments, the first manifold structure may be configured to rotate from the first position to the second position in response to the knob body being rotated relative to the housing to lock the proximal head to the instrument interface. In some embodiments, the second manifold structure may include a stopping surface configured to block the knob body from rotating beyond a predefined position to prevent separation of the knob body from the housing.

In some embodiments, a seal may include a proximally facing surface. A base structure may include a distally facing surface. The base structure may be configured to be axially translated toward the seal such that the seal and the base structure form a fluid-tight seal that is configured to prevent fluids from leaving an interior space and other interior regions of the apparatus, in response to the knob body being distally translated relative to the housing.

In some embodiments, the seal may be configured to deform against the distally facing surface of the base structure to form the fluid-tight seal. In some embodiments, the seal may include a stopping surface configured to block the knob body from rotating beyond a predefined position to prevent separation of the knob body from the housing.

In some embodiments, the housing may be a proximal housing. The apparatus may further comprise a distal housing and a sealing unit disposed between the proximal housing and the distal housing, configured to form a fluid-tight seal with the plurality of engagement elements to prevent fluids from leaving an interior space and other interior regions of the apparatus.

In some embodiments, the plurality of engagement elements may be configured to extend through the sealing unit. In some embodiments, each engagement element of the plurality of engagement elements, when the plurality of engagement elements is coupled to the one or more actuators, may be further configured to be driven by an actuator of the one or more actuators to axially translate relative to the sealing unit to move the end effector.

In some embodiments, subsequent to locking the proximal head to the instrument interface, the knob body may be configured to be axially translated relative to the housing to allow the knob body to be rotated and separated from the instrument interface.

Also described here are apparatuses including instrument coupling (translation or rotation) plus sealing. In some embodiments, an apparatus may comprise a shaft including a proximal end and a distal end. The shaft may define a lumen extending between the proximal end and the distal end. An end effector may be disposed at the distal end of the shaft. A proximal head may be disposed at the proximal end of the shaft. The proximal head may include a housing and a knob body disposed proximal of the housing. A first sealing element may be configured to move relative to a second sealing element to form a fluid-tight seal that prevents fluids from leaving an interior space and other interior regions of the apparatus. The knob body may be configured to be distally translated and/or rotated relative to the housing to lock the proximal head to an instrument interface of a surgical robotic system and to cause the first sealing element to move relative to the second sealing element to form the fluid-tight seal.

In some embodiments, the knob body may be configured to be distally translated and subsequently rotated relative to the housing to lock the proximal head to the instrument interface. In some embodiments, the first sealing element may be a first manifold structure defining one or more ports. The second sealing element may be a second manifold structure defining one or more channels. The first manifold structure may be configured to rotate relative to the second manifold structure to form the fluid-tight seal.

In some embodiments, the first sealing element may include a distally facing surface, and the second sealing element may include a proximally facing surface. The first sealing element may be configured to be axially translated toward the second sealing element to form the fluid-tight seal. In some embodiments, the second sealing element may include a stopping surface configured to block the knob body from rotating beyond a predefined position to prevent separation of the knob body from the housing.

In some embodiments, the housing may be a proximal housing. The apparatus may further comprise a distal housing and a plurality of engagement elements. Each engagement element of the plurality of engagement elements may be coupled to the end effector via a force transmitting element disposed within the lumen and be configured to translate relative to the proximal housing and the distal housing to actuate the end effector in at least one degree-of-freedom. In some embodiments, a sealing unit may be disposed between the proximal housing and the distal housing, configured to form a fluid-tight seal with the plurality of engagement elements to prevent fluids from leaving the interior space and other interior regions of the apparatus. In some embodiments, each engagement element of the plurality of engagement elements may be configured to extend through the sealing unit.

Also described here are methods including inserting an instrument in a first configuration into an instrument interface of a surgical robotic system such that a proximal housing of the instrument is disposed within the instrument interface. The instrument in the first configuration has a knob that is rotationally locked relative to the proximal housing. A knob of the instrument may be pushed relative to the proximal housing to transition the instrument into a second configuration in which the knob is unlocked and can rotate relative to the proximal housing. While the instrument is in the second configuration, the knob may be rotated relative to the proximal housing to lock the instrument to the instrument interface and to couple a plurality of engagement elements of the instrument to one or more actuators of the surgical robotic system such that the one or more actuators can drive movement of the plurality of engagement elements to move the end effector in at least one degree-of-freedom.

In some embodiments, in response to pushing and/or rotating the knob relative to the proximal housing, an interior space and other interior regions of the instrument may be sealed. In some embodiments, sealing the interior space and other interior regions of the instrument may include moving a first sealing element relative to a second sealing element to form a fluid-tight seal therebetween that prevents fluids from leaving the interior space and other interior regions of the instrument.

In some embodiments, pushing and/or rotating the knob relative to the proximal housing to lock the instrument to the instrument interface may include pushing and/or rotating the knob relative to the proximal housing in a first direction. The method may further comprise pulling and/or rotating, when the instrument is locked to the instrument interface, the knob relative to the proximal housing in a second direction opposite the first direction to unlock the instrument from the instrument interface. Pushing and/or rotating the instrument in the knob in the second direction may unseal the interior space and other interior regions of the instrument such that a cleaning fluid can enter the interior space and other interior regions of the instrument to clean and/or sterilize the interior space and other interior regions of the instrument.

In some embodiments, rotating the knob relative to the proximal housing to lock the instrument to the instrument interface may include rotating the knob until an audible and/or haptic feedback is generated.

In some embodiments, the audible and/or haptic feedback may be generated in response to an arm disposed on one of the knob or the proximal housing interfacing with a corresponding structure disposed on the other of the knob or the proximal housing.

BRIEF DESCRIPTION OF THE DRAWINGS

FIG. 12 depicts another perspective view of a proximal housing of the surgical instrument of FIG. 7, showing a travel path for a knob body of the surgical instrument, according to embodiments.

FIG. 13A depicts a side cutaway view of the surgical instrument of FIG. 7 in a first configuration, according to embodiments.

FIG. 13B depicts a side cutaway view of the surgical instrument of FIG. 7 in a second configuration, according to embodiments.

DETAILED DESCRIPTION

Figure 1:
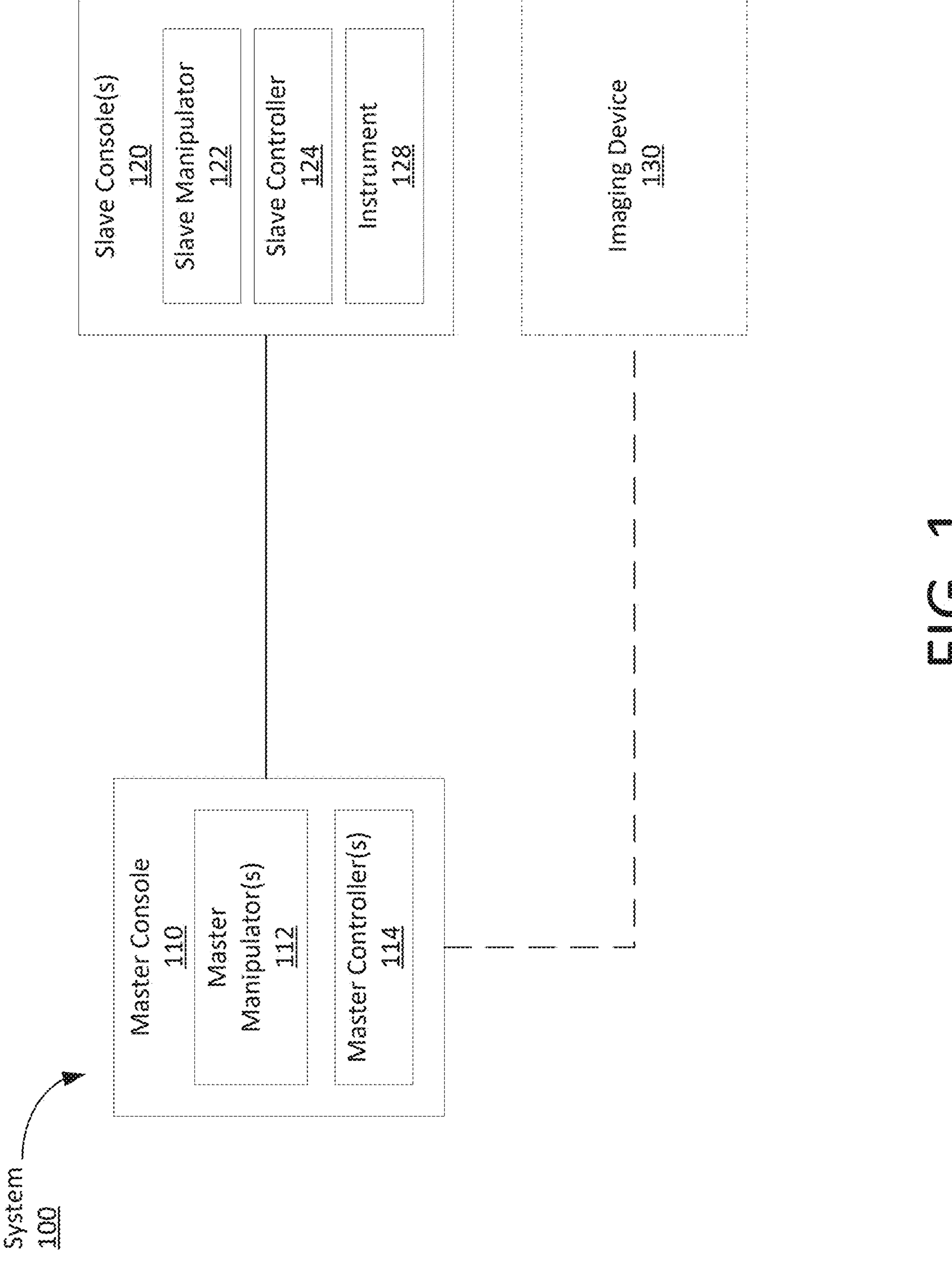
FIG. 1 schematically depicts a surgical robotic system, according to embodiments.

Described here are surgical instruments used in a surgical robotic system. These systems, devices, and methods may include mechanisms to removably couple a sterile instrument to a robotic arm while maintaining a sterile barrier. The systems, devices and methods described herein may, for example: improve ergonomics (e.g., usability) of the instrument using a push-to-turn feature that locks a knob of the instrument in a predetermined position for reinsertion into a sterile interface; provide a fluid-tight seal when the instrument is in-use based on an axial and rotational movement of the knob, thereby preventing fluid ingress into a hub of the instrument; and conversely provide fluid access to an interior space of the instrument when the instrument is not in-use to facilitate reprocessing and sterilization.

By contrast, conventional surgical instruments may not necessarily provide a knob of the instrument in a proper orientation for reinsertion into a sterile interface. Instead, the user may need to rotate the knob (e.g., rotate counter-clockwise) relative to the rest of the instrument until hearing an audible click corresponding to mechanical features that generate click sounds over corresponding features in the knob. Some users may find this operation undesirable or unintuitive.

Moreover, some conventional instruments include open channels at a proximal portion of the instrument that facilitate gas sterilization through an otherwise enclosed interior space of the instrument. If a fluid-tight seal at a distal portion of the instrument fails during a procedure, then undesirable fluid (e.g., liquid) may exit the instrument through the open channels and into other components of the system (e.g., sterile interface, hub) that may lead to contamination and/or failure of the system. However, fluid-tight seals at distal and proximal portions of the instrument may prevent sterilization using steam and/or ethylene oxide (EtO) gas. Conventional instruments do not allow openings to be formed without compromising fluid-tight seals of the instrument. As described in more detail herein, a knob of an instrument may be rotated to a first configuration to couple (e.g., mount) an instrument to a sterile interface, thereby forming a fluid-tight seal, and rotated to a second configuration to facilitate venting of the instrument for reprocessing and sterilization.

Generally, the apparatuses described here may provide instrument coupling with axial translation (e.g., pushing) and rotation. For example, an apparatus may comprise a shaft including a proximal end and a distal end. The shaft may define a lumen extending between the proximal end and the distal end. An end effector may be disposed at the distal end of the shaft. A proximal head may be disposed at the proximal end of the shaft. The proximal head may include a housing defining an internal space configured to house a plurality of engagement elements and a knob body disposed proximal of the housing. Each engagement element of the plurality of engagement elements may be coupled to the end effector via a force transmitting element disposed within the lumen. The knob body may be configured to be distally translated and subsequently rotated relative to the housing to lock the proximal head to an instrument interface of a surgical robotic system such that the plurality of engagement elements can be coupled to one or more actuators configured to drive movement of the plurality of engagement elements to move the end effector in at least one degree-of-freedom.

Also described here are apparatuses configured to provide instrument coupling (e.g., translation or rotation) with sealing. For example, an apparatus may comprise a shaft including a proximal end and a distal end. The shaft may define a lumen extending between the proximal end and the distal end. An end effector may be disposed at the distal end of the shaft. A proximal head may be disposed at the proximal end of the shaft. The proximal head may include a housing and a knob body disposed proximal of the housing. A first sealing element may be configured to move relative to a second sealing element to form a fluid-tight seal that prevents fluids from leaving an interior space and other interior regions of the apparatus. The knob body may be configured to be distally translated and/or rotated relative to the housing to lock the proximal head to an instrument interface of a surgical robotic system and to cause the first sealing element to move relative to the second sealing element to form the fluid-tight seal.

Also described here are methods of instrument coupling with axial translation (e.g., pushing) and rotation. For example, methods may include inserting an instrument in a first configuration into an instrument interface of a surgical robotic system such that a proximal housing of the instrument is disposed within the instrument interface. The instrument in the first configuration has a knob that is rotationally locked relative to the proximal housing. A knob body of the instrument may be pushed relative to the proximal housing to transition the instrument into a second configuration in which the knob body is unlocked rotationally and can rotate relative to the proximal housing. While the instrument is in the second configuration, the knob may be rotated relative to the proximal housing to lock the instrument to the instrument interface and to couple a plurality of engagement elements of the instrument to one or more actuators of the surgical robotic system such that the one or more actuators can drive movement of the plurality of engagement elements to move the end effector in at least one degree-of-freedom.

I. Systems and Devices

FIG. 1 schematically depicts a surgical robotic system 100, according to embodiments. The system 100 can include a master console 110 and one or more slave console(s) 120. Optionally, the system 100 can also include an imaging device 130, such as, for example, an endoscopic camera or other visualization device.

The master console 110 can be operatively coupled to the slave console(s) 120. For example, the master console 110 can be coupled to the slave console(s) 120 via wired and/or wireless connections. The master console 110 can include one or more master manipulator(s) 112 and one or more master controller(s) 114. In some embodiments, the master manipulator(s) 112 can include a plurality of master links that are interconnected by a plurality of joints. Movement can be applied to the master manipulator(s) 112 via a handle, which can be actuated by a user (for instance a sterile user, e.g., a surgeon). The movement of the master manipulator(s) 112 and one or more actuators of the handle can be sensed, e.g., using a plurality of sensors, and transmitted to the master controller(s) 114.

The master console 110 and the slave console(s) 120 can be examples of surgical robotic devices. In operation, the master console 110 can be configured to teleoperate the slave console(s) 120 to perform a surgical procedure. As further described below, movements of the master manipulator(s) 112 can be sensed at the master console 110, which can be translated into movements of portions of the slave console(s) 120.

Each slave console 120 can include a slave manipulator 122 and/or an instrument 128 (e.g., surgical instrument) that is coupled to the slave manipulator 122. The slave manipulator 122 can be implemented as a robotic arm, e.g., including a plurality of links that are interconnected by a plurality of corresponding joints. The slave console(s) 120 can include one or more drive units, actuators, or motors that control movement of the plurality of links and joints of the slave manipulator 122. The instrument 128 can be removably coupled to the slave manipulator 122. When the instrument 128 is coupled to the slave manipulator 122, the slave manipulator 122 can be configured to support the instrument 128 and to control its movements. In particular, the slave manipulator 122 can be configured to control and move the instrument 128 in a plurality of degrees of freedom (DOF), including translational and/or rotational movement. The slave manipulator 122 can be configured to control the movements of the instrument 128 in a manner responsive to movements applied at the handle of the master console 110. In particular, the master console 110 can generate instructions or commands based on movements applied at the handle and transmit those instructions or commands to the slave console(s) 120 to cause movement of the slave manipulator 122 and/or the instrument 128. The slave console(s) 120 can include a slave controller 124 that can be configured to interpret the instructions or other signals from the master console 110 and to control the movement of the slave manipulator 122 and/or the instrument 128.

While the slave console 120 is described as having a slave manipulator 122 and an instrument 128, it can be appreciated that a single slave console 120 can include more than one slave manipulator 122 and/or more than one instrument 128. For example, a slave console 120 can include two slave manipulators 122 that each support one or more instruments 128.

The master controller(s) 114 and the slave controller(s) 124, as described herein, can include one or more of a memory, a processor, a communications interface, and/or an input/output device. The memory can include any type of suitable non-transitory computer readable media that can store instructions that can be executed by one or more processors. The memory can be, for example, a random access memory (RAM), a memory buffer, a hard drive, a database, an erasable programmable read-only memory (EPROM), an electrically erasable read-only memory (EEPROM), a read-only memory (ROM), and/or so forth. The processor can be any suitable processing device configured to run and/or execute functions associated with the surgical robotic system 100. The processor can be a general purpose processor, a Field Programmable Gate Array (FPGA), an Application Specific Integrated Circuit (ASIC), a Digital Signal Processor (DSP), and/or the like. The communications interface can include wired and/or wireless interfaces for receiving information and/or sending information to other devices. The input/output device can include one or more displays, audio devices, touchscreens, keyboards, or other input or output devices for presenting information to and/or receiving information from a user.

Further examples of surgical robotic systems and instruments are described in PCT Patent Application No. PCT/IB2020/050039, filed Jan. 4, 2020, titled "Surgical Robot Systems Comprising Robotic Telemanipulators and Integrated Laparoscopy"; PCT Patent Application No. PCT/IB2019/050961, filed Feb. 6, 2019, titled "Surgical Robot Systems Comprising Robotic Telemanipulators and Integrated Laparoscopy"; and PCT Patent Application No. PCT/IB2023/060543, filed Oct. 19, 2023, titled "Pivot Joints for Surgical Cutting Devices, and Systems Thereof." The disclosures of each of the foregoing applications are incorporated by reference herein.

Figure 2:
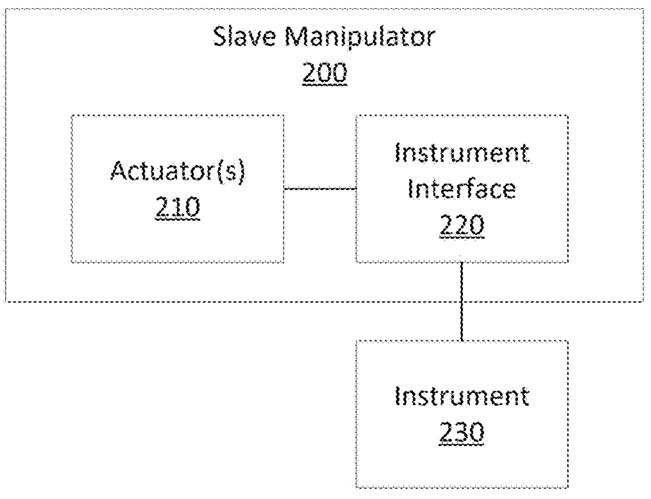
FIG. 2 schematically depicts a manipulator of a surgical robotic system, according to embodiments.

FIG. 2 schematically depicts a slave manipulator 200 of a slave console, according to embodiments. The slave manipulator 200 can include an actuator 210 and an instrument interface 220. The actuator(s) 210 can include one or more electric actuators (e.g., motors), mechanical actuators (e.g., pulleys, chains, gears, shafts, etc.), or other drive mechanisms that are configured to actuate or move one or more components of the slave manipulator 200 and/or other components connected thereto. For example, the actuator(s) 210 can be configured to move the plurality of links and joints of the slave manipulator 200, the instrument interface 220, and/or one or more component(s) of the instrument 230. The instrument 230 can be coupled to the actuator 210 via the instrument interface 220. In some embodiments, the instrument interface 220 can include a hub for receiving the instrument 230. The hub can be mounted on the distal end of the slave manipulator 200, and define an opening for receiving the instrument 230. In some embodiments, the instrument interface 220 can include or be coupled to a sterile adapter or shield. The sterile adapter can be configured to be received within the hub, and can define a lumen for receiving a sterile instrument 330. Suitable examples of instrument hubs and sterile shields are described with reference to PCT Patent Application No. PCT/IB2018/053272, filed May 11, 2018, titled "Translational instrument interface for surgical robot and surgical robot systems comprising the same," and incorporated herein by reference. The instrument 230, when coupled to the instrument interface 220, can be moved by one or more actuator(s) 210, e.g., in one or more degrees of freedom. In some embodiments, the instrument interface 220 may be configured to receive more than one instrument 230.

Figure 3:
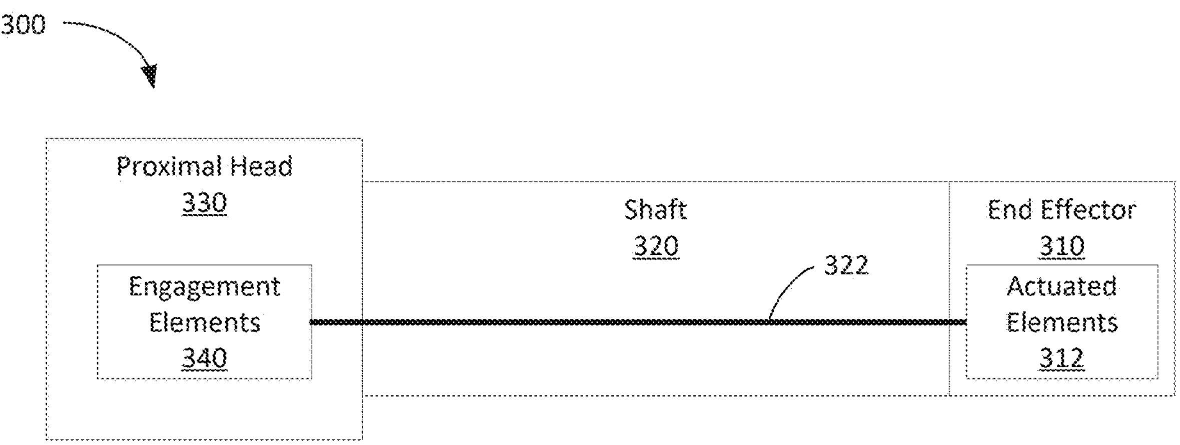
FIG. 3 schematically depicts the instrument of the surgical robotic system of FIG. 2, according to embodiments.

FIG. 3 schematically depicts an instrument 300 (e.g., a surgical instrument of a surgical robotic system, such as, for example, surgical robotic system 100), according to embodiments. The instrument 300 can include a proximal head 330, a shaft 320, and a distal end effector 310. The proximal head 330 can be configured to couple to the instrument interface (e.g., instrument interface 220, as shown in FIG. 2). The proximal head 330 can include one or more engagement elements or engagement elements 340 (e.g., engagers). The engagement elements 340 can be coupled to one or more transmission members 322 (e.g., force transmitting elements such as cables, wires, pulleys, rods, etc., or electrical transmitting elements such as wires, leads, electrodes, etc.) disposed in the shaft 320 of instrument 300. The shaft 320 can be an elongate structure, e.g., an elongate cylinder. The shaft 320 can define a lumen (or plurality of lumens) for housing the transmission member 322.

In embodiments, the engagement elements 340 include one or more extensions, protrusions, latches, tabs, hooks, ports, electrical contacts, or other suitable structure that can be configured to engage with corresponding structure of the instrument interface 220. In an embodiment, the engagement elements 340 can include radially extending tabs that are configured to be received in receptacles disposed in a hub of the slave manipulator 200. The receptacles can be driven by the actuator(s) 210 to move, to thereby transmit forces to the engagement elements 340. Examples of suitable engagement elements (or engagers) and receptacles are described in PCT Patent Application No. PCT/IB2018/053272, incorporated above by reference. While engagement elements and receptacles are described with reference to FIG. 2, it can be appreciated that any suitable form of coupling that allows the actuator(s) 210 of the slave manipulator to couple to one or more actuated elements 312 of the end effector 310 to thereby actuate the actuated elements 312 in one or more degrees of freedom can be used. For example, in some embodiments, the coupling between the instrument interface 220 and the instrument 300 can include a mechanical coupling (e.g., latches, pin and hole, grippers, fasteners, etc.), a magnetic coupling (e.g., electromagnets, permanent magnets, etc.), and/or an electrical coupling.

The end effector 310 can be a surgical tool, such as, for example, a set of jaws, a clamp, a grasper (e.g., bipolar Johann grasper, bipolar Maryland dissector, needle holder), a blade, a scissor, a hook, a needle, a stapler, an electrocautery device, an endoscope, and the like. The end effector 310 can include one or more actuated elements 312, e.g., one, two, three, four, five, six, seven, eight, or more actuated elements. The actuated elements 312 can be configured to be actuated (e.g., driven to move or otherwise operate) by the actuator(s) 210 via the engagement element 340 and the transmission elements 322. For example, the actuated elements 312 can include jaws, clamps, or cutting elements that can be actuated in one or more degrees of freedom, e.g., open/close, pitch, yaw, translation, etc.

In an embodiment, the end effector 310 can be a surgical scissor that includes a pair of jaws or cutting members. Accordingly, the one or more actuated elements 312 may move (e.g., rotate, pivot, translate) in one or more degrees of freedom. In embodiments with a plurality of actuated elements (e.g., two actuated elements), the movement of the actuated elements relative to each other may facilitate opening and/or closing the end effector 310. For example, a first actuated element may be moved (e.g., rotated) in a direction towards a second actuated element, such that cutting portions of the actuated elements may come into contact. According to some embodiments, each of the actuated elements can move toward or away from each other. In yet further embodiments, each of the actuated elements may be moved together in the same direction, such that the actuated elements may maintain an opening angle defined therebetween. The direction and magnitude of movement of the end effector 310 can be controlled via forces applied to the engagement elements 340 by one or more actuator(s) 210. The movement of the end effector 310 can provide adjustability and flexibility to the user while performing a cutting process. Further details of surgical tools with two actuating members are described in PCT Patent Application No. PCT/IB2023/060543, incorporated above by reference.

Figure 4:
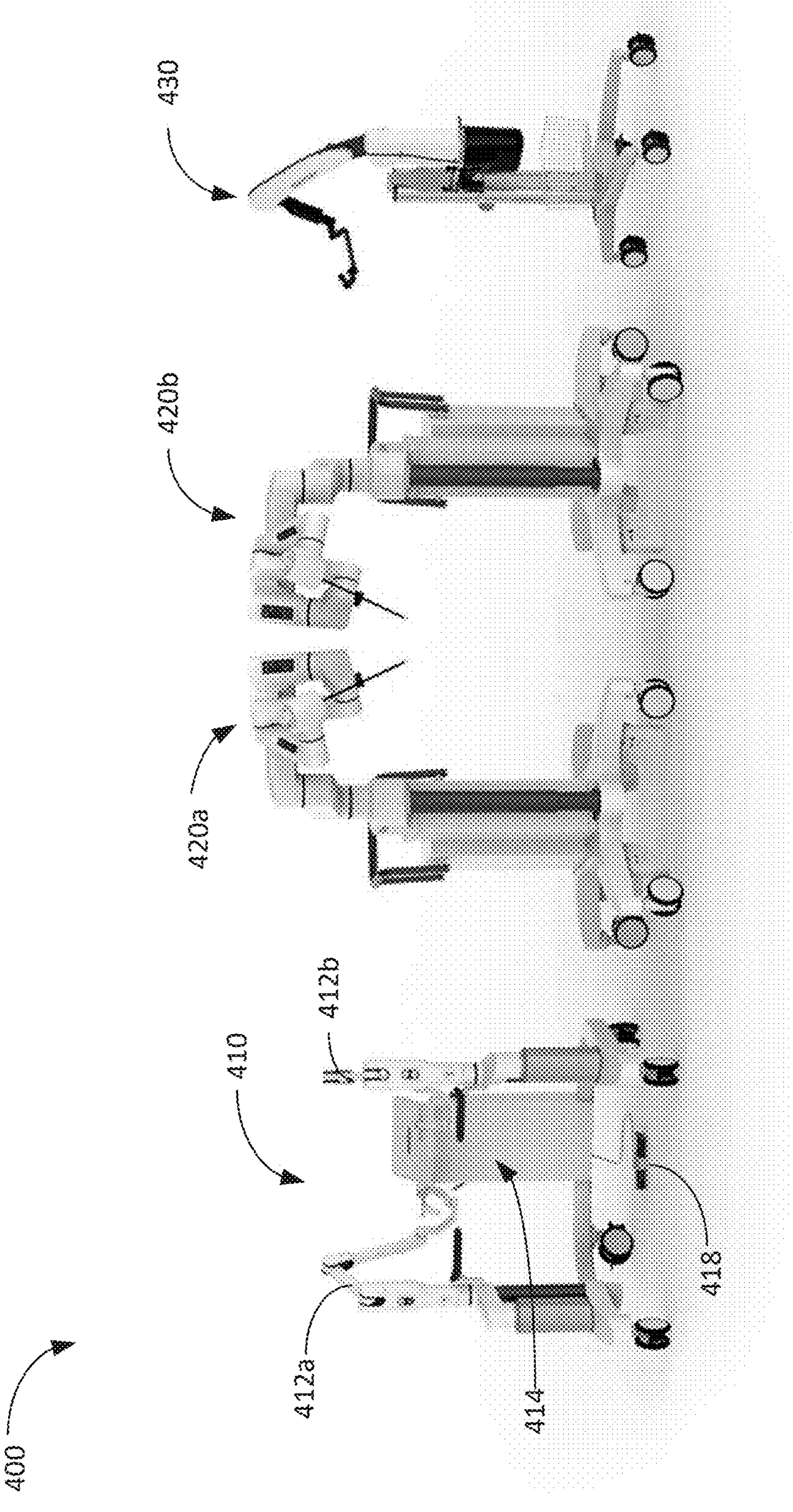
FIG. 4 shows an example surgical robotic system including a master console and multiple slave manipulators, according to embodiments.

FIG. 4 depicts an example of a surgical robotic system 400, according to embodiments. The surgical robotic system 400 can be structurally and/or functionally similar to other surgical robotic systems described herein, including, for example, the surgical robotic system 100, and therefore can include components that are structurally and/or functionally similar to the components of such other systems. For example, the surgical robotic system 400 can include a master console 410 including two master manipulators 412*a* and 412*b* (e.g., left and right manipulators) and a master controller 414, two slave consoles 420*a*, 420*b* (e.g., left and right slave consoles), and an imaging device implemented as an endoscope device 430.

In operation, movement of the first slave manipulator 412*a* (and handle coupled thereto) can be sensed and transmitted to the master controller 414, which can then send instructions to a first slave console 420*a* to control the movement of the first slave console 420*a*. Similarly, movement of the second slave manipulator 412*b* (and handle coupled thereto) can be sensed and transmitted to the master controller 414, which can then send instructions to a second slave console 420*b* to control the movement of the second slave console 420*b*. In some embodiments, the master console 410 can also include one or more foot pedal(s) 418 or other actuator(s), which can be depressed to engage or release a clutch. When the clutch is engaged (e.g., by depressing one or more foot pedal(s) 418), the master controller 414 can be configured to send instructions that cause the slave consoles 420*a*, 420*b* to replicate movements of the master manipulators 412*a*, 412*b*. And when the clutch is not engaged, the master controller 414 may pause sending instruction to the slave consoles 420*a*, 420*b*, such that the slave consoles 420*a*, 420*b* do not replicate the movements of the master manipulators 412*a*, 412*b* and/or deactivate the movement of the slave console(s) 420*a*, 420*b* in some other manner.

Surgical Instruments

Figure 5:
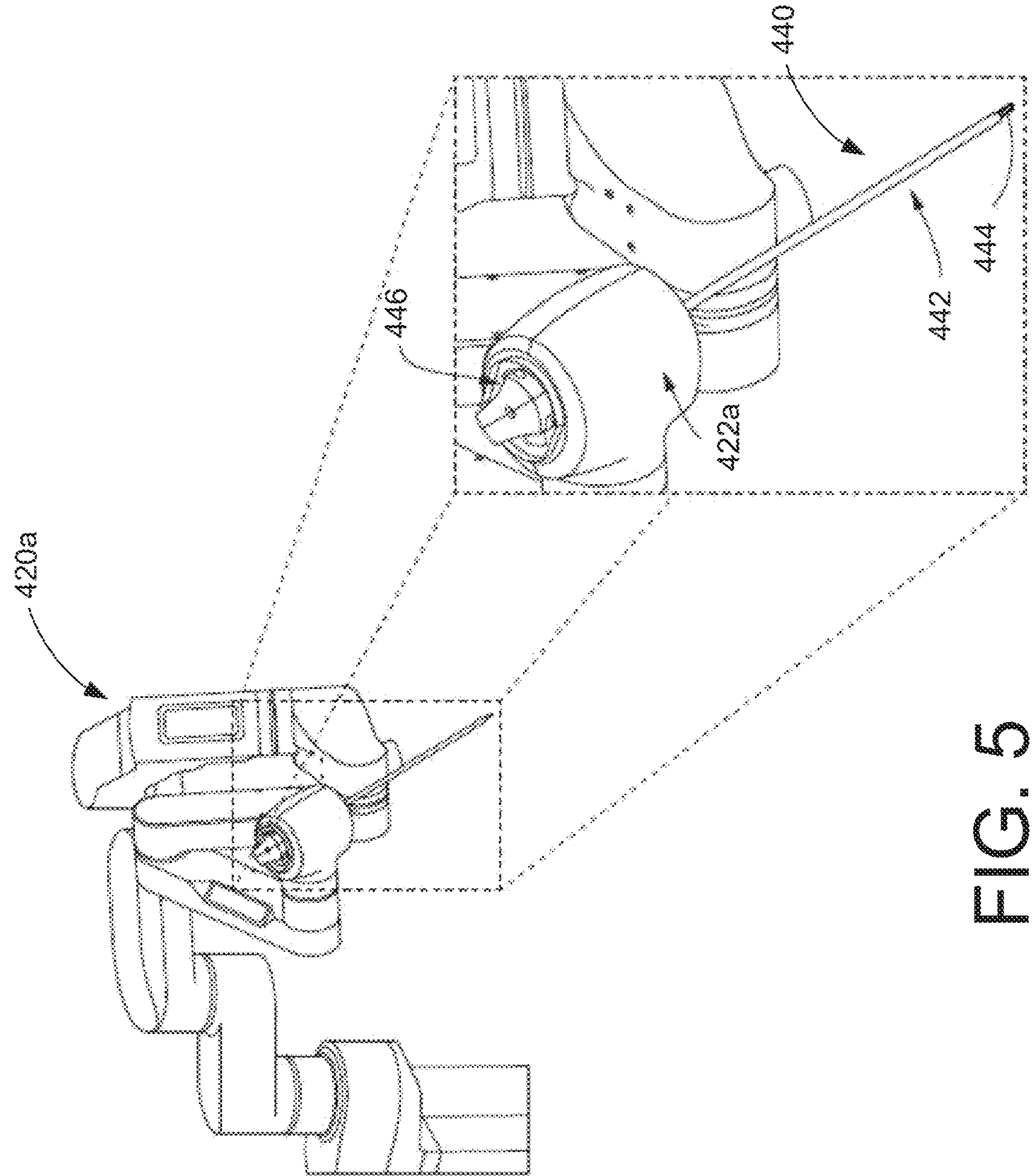
FIG. 5 depicts a detailed view of an instrument coupling of a surgical robotic system, according to embodiments.

FIG. 5 provides a close-up view of an instrument 440 positioned in a hub of a slave manipulator of a slave console 420*a*, according to embodiments. As shown in FIG. 5, the instrument 440 has a proximal head 446, a shaft 442, and a distal end effector 444. The instrument 440 can be structurally and/or functionally similar to other instruments described herein, including for example, instrument 128, 230, 330, 600, 700, 800. The proximal head 446 of the instrument 440 can be releasably coupled to a hub or instrument interface 422*a* of the slave manipulator. The hub 422*a* can define an opening through which the instrument 440 can be inserted. The instrument 440, after being inserted into the hub 422*a* and coupled to the slave manipulator, can be configured to be actuated in one or more degrees of freedom, as described above.

Figure 6:
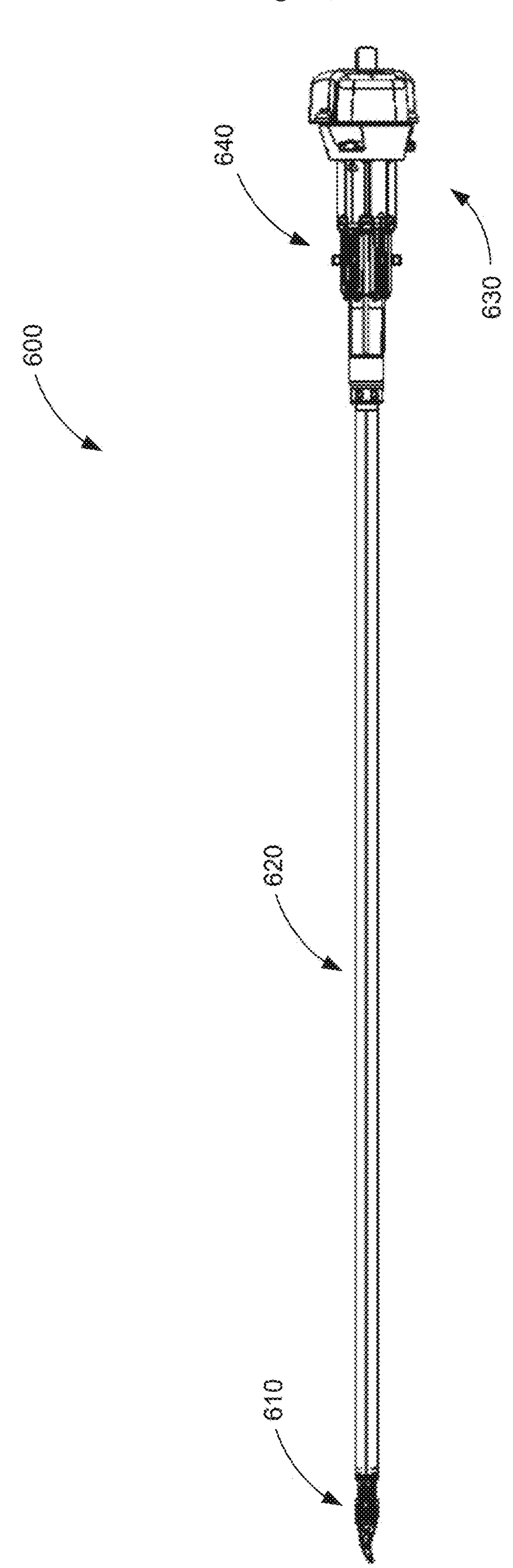
FIG. 6 depicts a surgical instrument of a surgical robotic system, according to embodiments.

Referring now to FIG. 6, an example surgical instrument 600 is provided. The surgical instrument 600 can be structurally and/or functionally similar to other instruments described herein, including, for example instruments 128, 230, 330, 440, 700, 800. Surgical instrument 600 may include a proximal region including an instrument head or proximal head 630, a distal region having an end effector 610, and an instrument shaft 620 extending between the proximal region and the distal region. In some embodiments, the end effector 610 may be removable from the shaft 620. In some embodiments, the shaft 620 may be removable from the head 630 and/or end effector 610.

As shown in FIG. 6, the instrument 600 may include one or more engagement elements (e.g., pairs of engagers) 640 configured to be actuated to actuate end effector 610 in one or more degrees of freedom, e.g., pitch, yaw, and open/close. For example, engagers 640 may be operatively coupled to end effector 610 via a plurality of force transmitting elements, e.g., cables, extending from engagers 640 through instrument shaft 620 to end effector 610. In some embodiments, pairs of engagers of engagers 640 may be actuated to actuate one or more components of end effector 610, e.g., in pitch and/or yaw degrees of freedom. The one or more pairs of engagers 640 may be removably engaged with corresponding structures of a hub of a slave console (e.g., slave console 120), e.g., via a releasable hook mechanism, such that movements at a handle of a master console (e.g., operated by a surgeon) may be replicated at end effector 610 of surgical instrument 600.

In some embodiments, an instrument may be configured to couple to a sterile interface using axial translation (e.g., pushing) and rotational movement. The instrument may improve user experience with preparing and coupling an instrument to an interface or hub of a surgical robotic system. The instrument may also be designed to automatically seal an instrument when the instrument is coupled to the surgical robotic system, for use in performing a surgical procedure, and/or be designed to automatically unseal the instrument when the instrument is decoupled and removed from the surgical robotic system. The instruments can be reusable instruments, e.g., instruments that are designed to be used in more than one surgical procedure, and can be disinfected or sterilized before each procedure. Alternatively, the instruments can be single-use instruments or disposable instruments, e.g., instruments that are designed to be used in a single procedure and discarded. In both types of instruments, it can be important to sterilize an interior space or internal components of the instrument, as further described below. The interior space and other interior regions of an instrument can include, for example, those portions of the instrument (e.g., surfaces, components, or portions thereof) that are not exposed to an external environment, not disposed on an exterior of the instrument, and/or not visible from an external view of the instrument. The internal components of the apparatus can include components that include at least a portion that is internally housed and not exposed to an external environment of the instrument. In some cases, an internal component can be entirely housed within exterior portions of the instrument. In some cases, an internal component can include portions that are housed within an exterior of the instrument, but also include portion(s) or surface(s) that are externally facing (e.g., exposed to the external environment).

Reusable Instrument

FIGS. 7-17B depict an example of an instrument 700 of a surgical robotic system, according to embodiments. The instrument 700 can be a reusable instrument, e.g., an instrument that can be used in multiple surgical procedures. Therefore, the instrument 700 can be configured to be sterilized prior to each use of the instrument 700.

Figure 7:
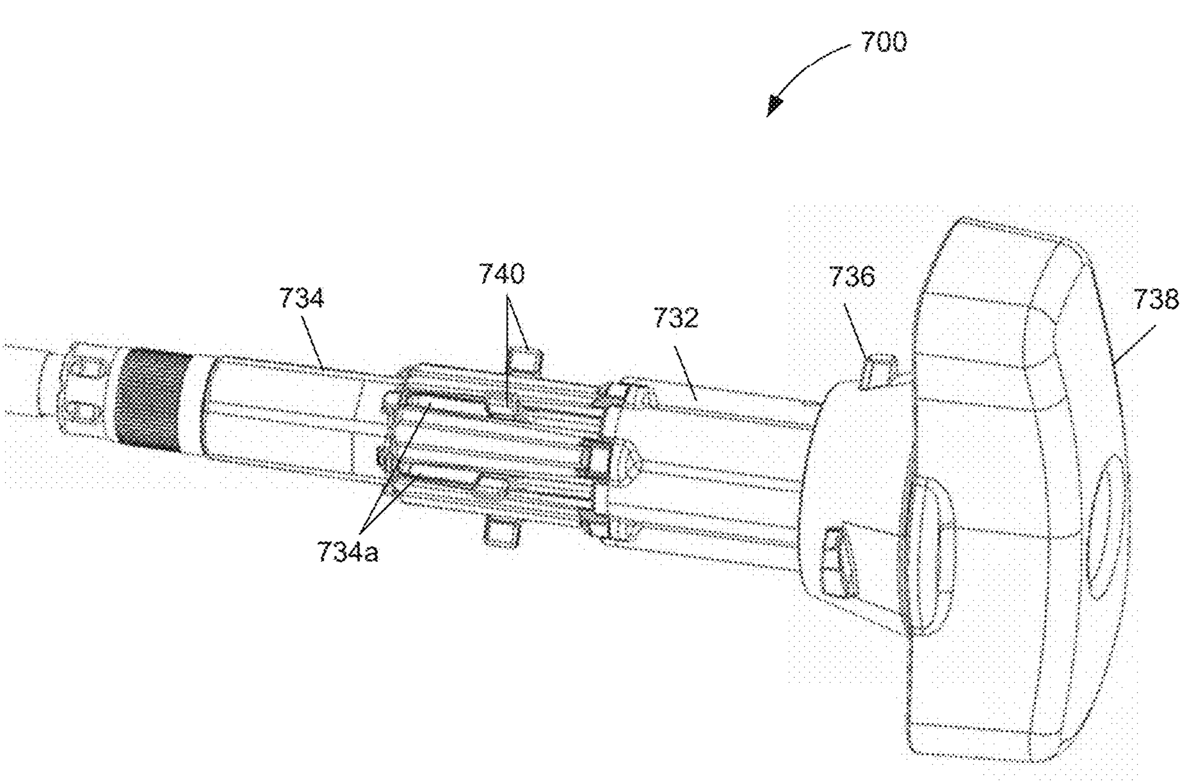
FIG. 7 depicts a perspective view of a proximal end of a surgical instrument of a surgical robotic system, according to embodiments.

FIG. 7 depicts a perspective view of a proximal end of the instrument 700. The instrument 700 can be functionally and/or structurally similar to other instruments described herein, including the instrument 600, and therefore can include similar components as such instruments. For example, the instrument 700 may include a shaft (e.g., similar to shaft 620) including a proximal end and a distal end. The shaft may define a lumen extending between the proximal end and the distal end. An end effector (e.g., end effector 610) may be disposed at the distal end of the shaft. A proximal head (e.g., proximal head 630) may be disposed at the proximal end of the shaft. As shown in FIG. 7, the proximal head may include one or more housings (e.g., a proximal housing 732 and a distal housing 734) defining an internal space or lumen configured to house a plurality of engagement elements 740, and a knob disposed proximal of the housings. The knob may comprise a knob body 736 and a knob cover 738 coupled to and proximal to the knob body 736. Each engagement element of the plurality of engagement elements 740 may be coupled to the end effector via cables 722 (e.g., force transmitting elements) disposed within the lumen.

As described in more detail herein, the knob body 736 may be configured to be distally translated and subsequently rotated relative to the housing 732 to lock the proximal head to an instrument interface of a surgical robotic system such that the plurality of engagement elements 740 can be coupled to one or more actuators configured to drive movement of the plurality of engagement elements 740 to move the end effector in at least one degree-of-freedom. In some embodiments, each engagement element of the plurality of engagement elements 740 may be configured to translate relative to the proximal housing 732 and the distal housing 734 to actuate the end effector in at least one degree-of-freedom.

Figure 8:
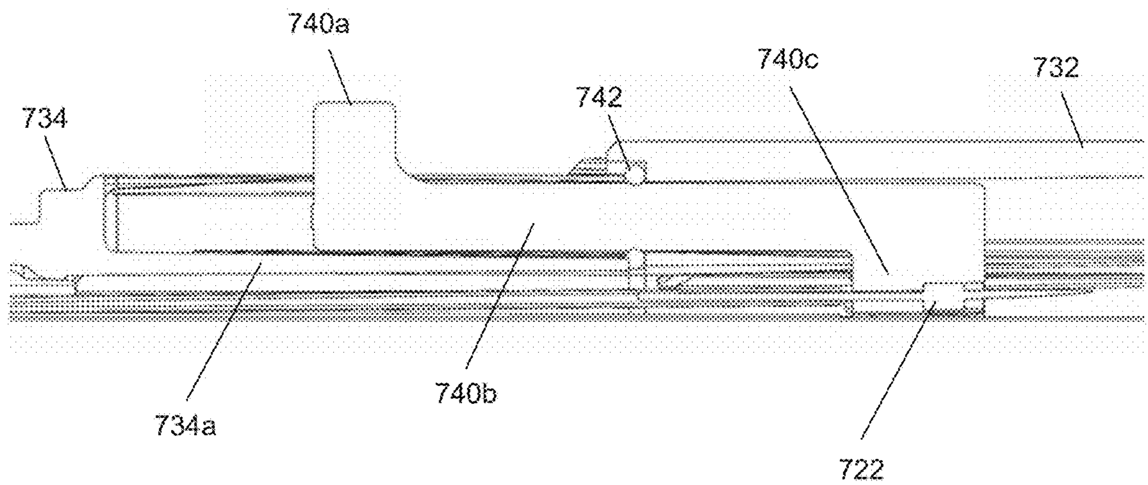
FIG. 8 depicts a close-up, cross-sectional view of a portion of the surgical instrument of FIG. 7, according to embodiments.

As shown in the detailed cross-sectional side view of FIG. 8, the instrument 700 may include a plurality of slots 734*a* disposed circumferentially or peripherally around a longitudinal axis of the instrument 700. The plurality of engagement elements 740 may be disposed in the slots 734*a*, e.g., with each engagement element 740 disposed within a separate slot of the plurality of slots. Each engagement element 740 may include an engagement portion 740*a*, an elongate portion 740*b*, and a cable coupling portion 740*c*. The engagement portion 740*a* can be configured to engage with one or more receptacles, as described above, to couple the engagement element 740 to one or more drive units of a surgical robotic system. The cable coupling portion 740*c* can be configure to couple the engagement element 740 to a proximal end of a cable 722 of a plurality of cables. The cables 722 can then be coupled at their distal end to one or more end effector components, e.g., to drive movement of the end effector, as described above. Each engagement element 740 also includes an elongate portion 740*b* that is configured to fit within the slot and connect the engagement portion 740*a* to the cable coupling portion 740*c*. The slots 734*a* can be defined by or between the proximal housing 732 and the distal housing 734. In some embodiments, the slots 734*a* can be linear slots or channels, and can define a passageway within which each engagement element 740 can move to translate relative to the proximal housing 732 and the distal housing 734, e.g., to actuate the end effector in at least one degree-of-freedom.

Further, as shown in FIG. 8, a sealing unit 742 may be disposed in the slots 734*a*, e.g., between the proximal housing 732 and the distal housing 734. The sealing unit 742 may be configured to form a fluid-tight seal with the plurality of engagement elements 740 to prevent fluids from exiting or leaving an interior space and other interior regions of the instrument 700. The sealing unit 742 can include, for example, one or more seals or sealing devices. During operation of the instrument, e.g., during surgery, fluids such as bodily fluids may enter an interior space of the instrument 700, e.g., via spaces or openings near a distal end of the instrument 700 (e.g., at or near the end effector). These fluids may travel proximally along the length of the instrument 700 (e.g., along a shaft of the instrument) and reach the proximal head of the instrument 700. If the fluids were allowed to exit from the proximal head of the instrument 700 while the instrument is coupled to the instrument interface of a surgical robotic system, the fluids may reach electronic circuitry or other components of the surgical robotic system and damage those components. To prevent this, the sealing unit 742 can be configured to seal around the engagement elements 740 and between the distal and proximal housings 732, 734 of the instrument to prevent egress of the fluid toward the instrument interface and electronic circuitry of the surgical robotic system. As such, the sealing unit 742 permits assembly of the elements of the housing (e.g., the distal and proximal housing 732, 734) in a leak-tight manner. The engagement elements 740 can be configured to extend through the sealing unit 742, such that the engagement portions 740*a* of the engagement elements 740 can be engaged with one or more actuators of the robotic system while the cable coupling portions 740*c* are coupled to the cables 722. The engagement elements 740 can move relative to the sealing unit 742, e.g., in an axial direction. The engagement elements 740, by being extended through the sealing unit 742, can remain leak-tight while moving in an axial direction.

The instruments described herein (e.g., instruments 600, 700, 800, and/or other instruments described herein) may have a push-to-turn functionality where, after inserting the instrument into a sterile interface, a user may press a knob distally relative to other portions of the instrument (e.g., a proximal housing of the instrument) to allow the knob to rotate and lock the instrument into the sterile interface. Prior to being inserted into the sterile interface, the knob can be prevented from rotating relative to other portions of the instrument, e.g., to prevent the knob from rotating out of position for insertion into the sterile interface. This is important as the instruments described herein must be placed into specific configurations for insertion into an instrument interface of a surgical robotic system. The knob of the instrument must be in an initial configuration relative to other portions of the instrument to enable locking and/or coupling of the instrument to the instrument interface and appropriate engagement of the engagement elements with the receptables and actuators of the robotic system.

Additionally, prior to each use of the instrument, it may be necessary to sterilize the instrument. Therefore, one or more openings (e.g., passages, channels, ports, etc.) into an interior space of the instrument must be provided, e.g., to allow cleaning or sterilization fluids to be injected or otherwise delivered into the interior of the instrument. The cleaning fluids can sterilize the interior space and/or internal components of the instrument, and/or fluid out any debris, bodily fluids, or other contaminants from the interior space of the instrument. Then during use (e.g., in a surgical operation), the instrument is sealed (e.g., via manifolds, sealing devices, and/or other components described herein) to prevent bodily fluids that have entered the interior space of the instrument from exiting the instrument (which, as described above, it beneficial to prevent those fluids from coming into contact with sensitive electronic circuitry or other components of the surgical robotic system). Therefore, the instruments described herein can be in a first configuration (e.g., a vented configuration) that allows for sterilization (e.g., delivery of a cleaning fluid into the interior space) and then be reconfigured during use to seal in the interior space of the instrument. The instruments can be reconfigured by rotating the knob of the instrument relative to other portions of the instrument, as described herein.

Figure 22:
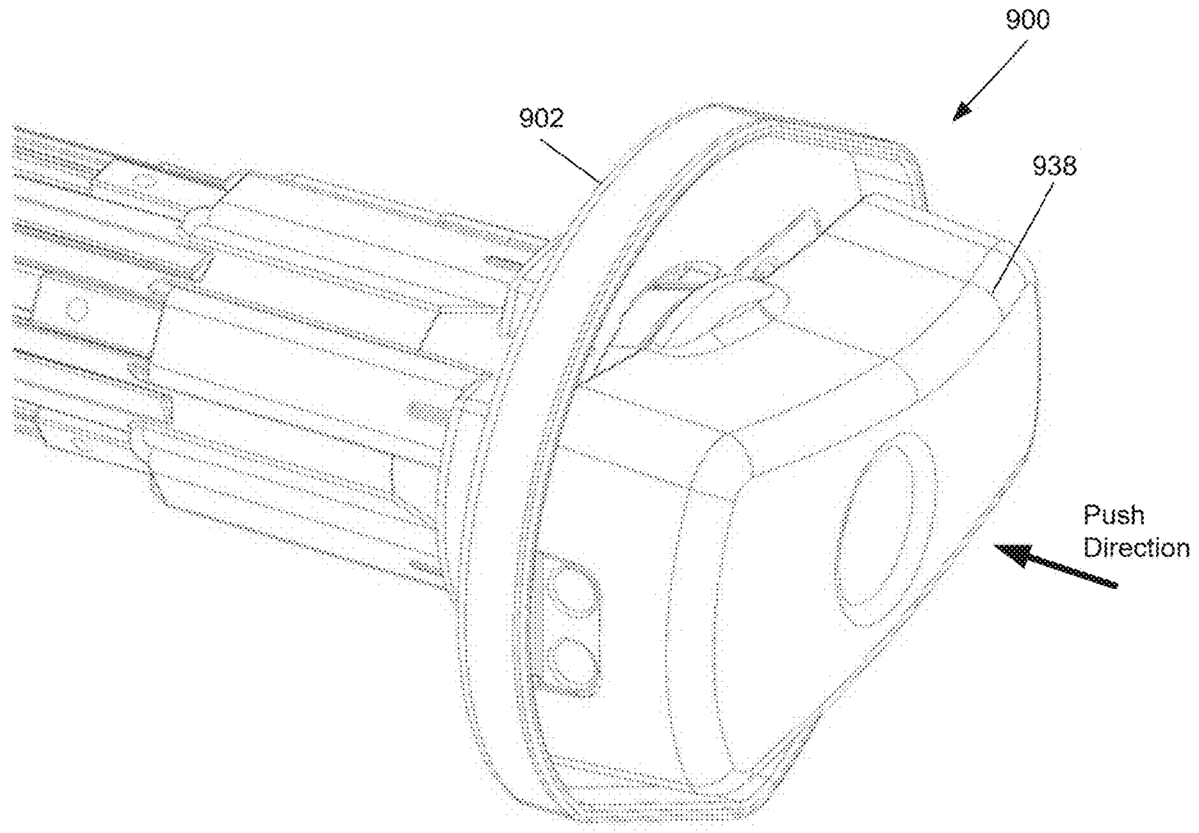
FIG. 22 depicts a perspective view of a sterile interface and a surgical instrument of a surgical robotic system, according to embodiments.
Figure 23:
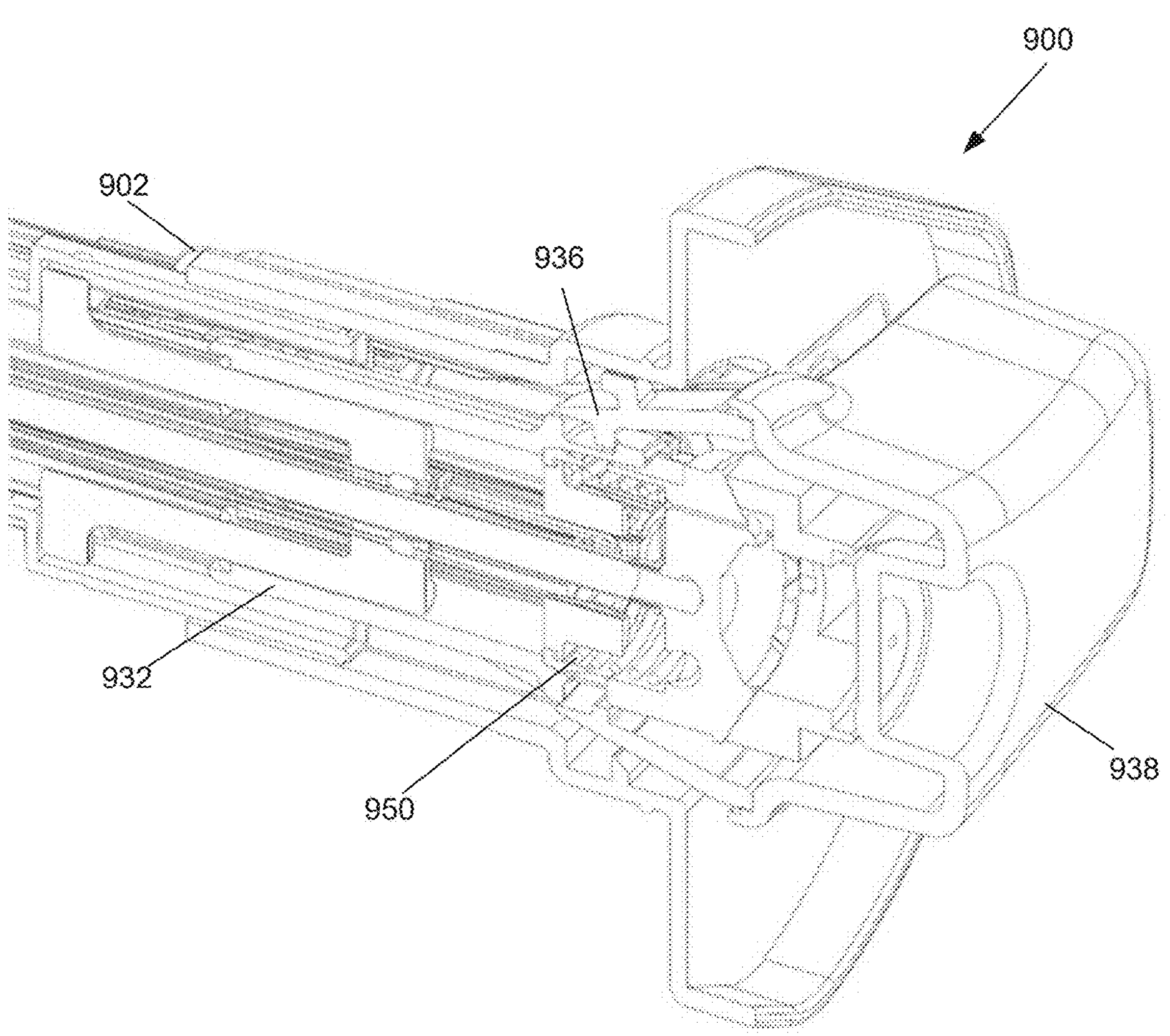
FIG. 23 depicts a cross-sectional perspective view of a sterile interface and a surgical instrument of a surgical robotic system, according to embodiments.
Figure 24:
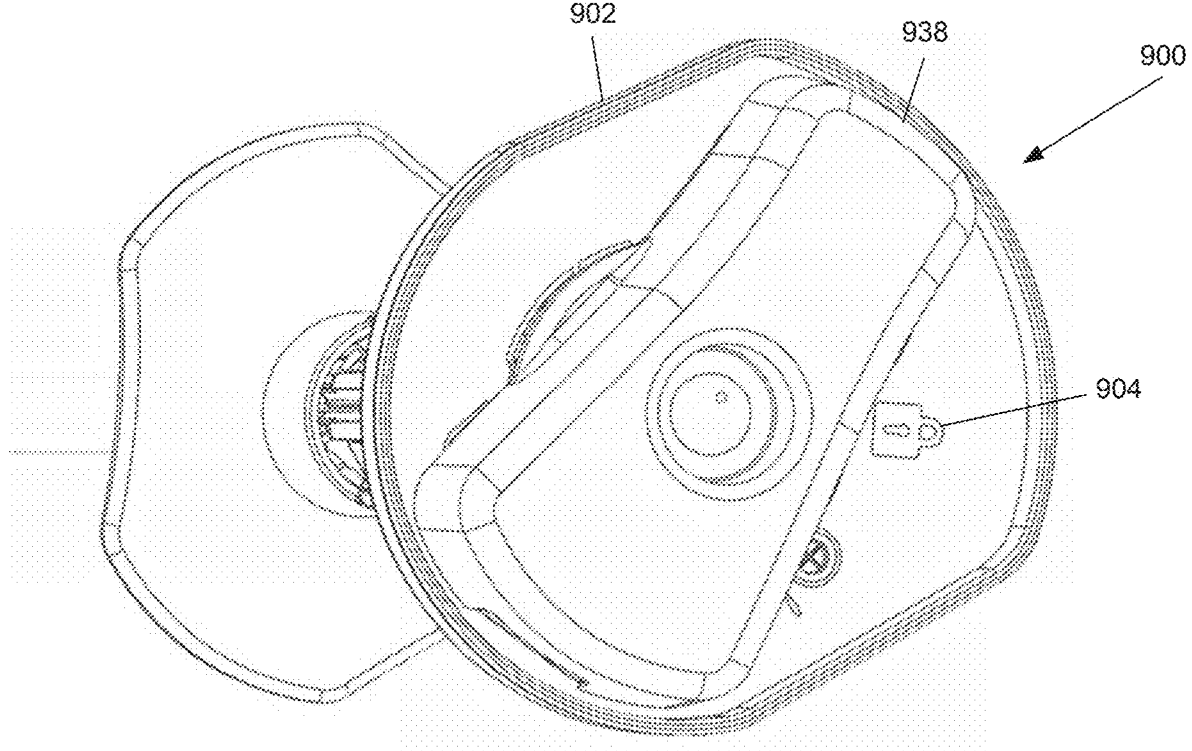
FIG. 24 depicts a rear perspective view of a sterile interface and a surgical instrument of a surgical robotic system in a first configuration, according to embodiments.

In more detail, an instrument 900 (e.g., structurally and/or functionally similar to other instruments depicted herein) may be inserted into a lumen of the sterile interface 902 and a knob cover 938 (e.g., structurally and/or functionally similar to knob cover 738, 838) may be pushed axially in a distal direction, as shown in the perspective view of FIG. 22. As shown in FIG. 23, the instrument may include a proximal housing 932, a knob body 936, and a spring 950. FIG. 24 depicts a rear perspective view of the knob cover 938 of the instrument 900 when it has initially been inserted into the sterile interface 902. When the instrument 900 is being inserted into the sterile interface 902, as shown in FIGS. 22-24, the instrument 900 can be in a first configuration (e.g., a configuration in which the interior space of the instrument is not sealed in). The spring 950 of the instrument can be configured to bias the knob body 936 proximally in the axial direction into a position that prevents its rotation relative to the proximal housing 932 of the instrument. Thereafter, the instrument can be pushed distally relative to the sterile interface 902.

Figure 25:
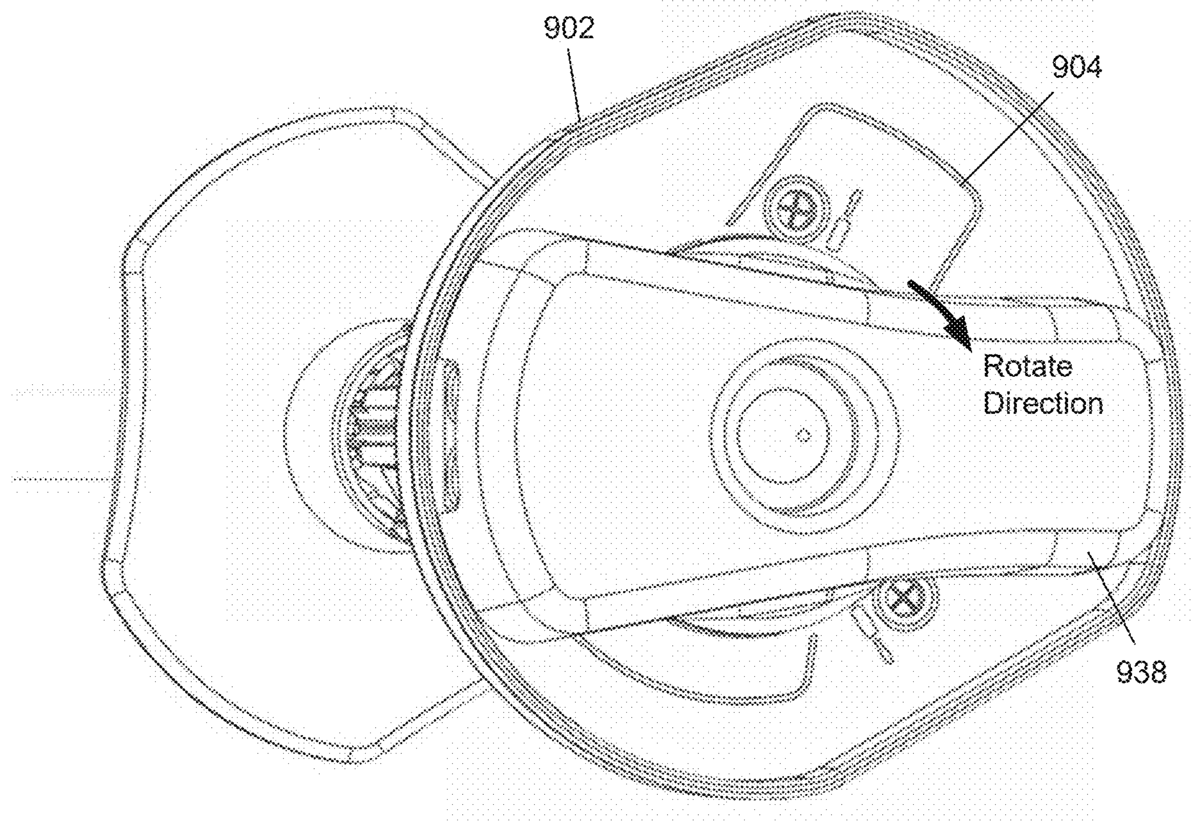
FIG. 25 depicts another rear perspective view of a sterile interface and a surgical instrument of a surgical robotic system in a second configuration, according to embodiments.

A user can press on the knob body 936 to overcome the force of the spring to move the knob body 936 (and other portions of the knob) distally relative to the sterile interface and proximal housing 932 of the instrument 900. A visual indicator such as a lock indicator 904 is visible in the pushed-in configuration to indicate the direction in which the knob cover 938 should be rotated in order to lock the instrument 900 into position with respect to the sterile interface 902. As shown in FIG. 25, the user is able to rotate the knob cover 938 (e.g., in a clockwise direction, though the arrangement can be in an opposite direction without departing from the scope of the present disclosure) relative to the sterile interface 902 until reaching a rotational stop (not shown in FIG. 25, however described in figures below) which secures (e.g., locks, mechanically couples) the instrument 900 to the sterile interface 902. The instrument 900 in FIG. 25 is in a second configuration (e.g., an in-use configuration) where the instrument is configured to be operated with the robotic surgical system and the interior space of the instrument has been sealed off from the external environment (e.g., one or more fluid passageways have been closed). An insertion position indicator 904 may be visible when the instrument 900 and sterile interface 902 are in the second configuration. The instrument, as coupled to the sterile interface 902, can then be used to perform a procedure (e.g., a surgical procedure). When the instrument needs to be decoupled from the surgical robotic system and the sterile interface 902, the user can rotate the instrument back toward its first configuration, to unlock the instrument and remove it from the sterile interface. When the user rotates back to the first configuration, the spring 950 can bias the knob cover 938 proximally so as to prevent rotational movement of the knob cover 938. Therefore, the instrument 900 may again be in a configuration for sterilization, but also in a configuration in which the instrument 900 can readily be reinserted into the sterile interface 902, e.g., for performing additional portions of the procedure. As such, the instrument can be reinserted into the sterile interface 902 without performing any additional actions, thereby providing a natural and intuitive process. In some procedures, such removal and reinsertion of the instrument into the sterile interface may be necessary, either owing to an operator having misaligned or improperly inserted the instrument in a first pass, or due to different instruments being swapped in and out of the instrument interface during the procedure (e.g., due to performing different portions of the procedure). For example, in a surgical procedure, a physician may desire to swap out a first instrument such as a pair of jaws for a second instrument such as a needle or hook, or other type of instrument, depending on the protocol or requirements of the particular procedure.

While certain indicators are shown with reference to FIGS. 24 and 25, it can be appreciated that other types of indicators can be used without departing from the scope of the present disclosure. For example, visual, audio, and/or haptic indicators can be used to guide an operator in inserting an instrument and rotating it to lock to the surgical robotic system.

Figure 9:
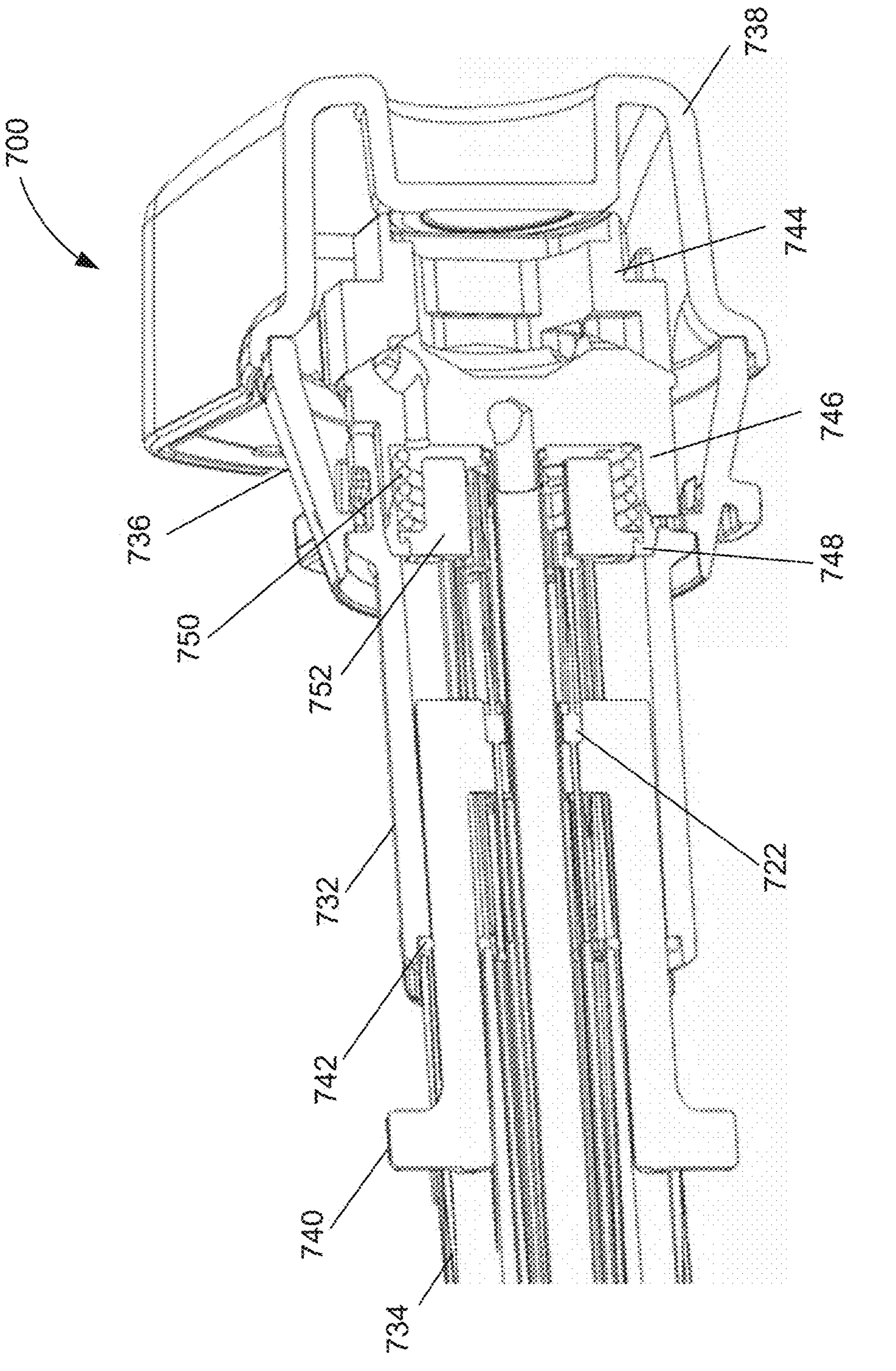
FIG. 9 depicts a cross-sectional view of a proximal end of the surgical instrument of FIG. 7, according to embodiments.

Referring now back to FIGS. 7-17B, more details are provided regarding the push-to-turn and sealing features of instrument 700. FIG. 9 depicts a cross-sectional side view of the proximal end of the instrument 700. Similar to instrument 900, the instrument 700 can be configured to transition between a first configuration, in which the instrument 700 is ready for insertion into a sterile interface (e.g., sterile interface 902) of a surgical robotic system, and a second configuration, in which the instrument 700 is locked to the sterile interface. In the first configuration, the instrument 700 can be vented, e.g., unsealed and open to allow for fluid (e.g., cleaning fluid) entry into the interior space of the instrument for sterilization and/or reprocessing of the instrument. And in the second configuration, the instrument 700 can be sealed or closed off (i.e., not vented), e.g., to prevent egress of fluid (e.g., bodily fluid) out of the interior space of the instrument.

The instrument 700 can be configured to operate via push-to-turn operation using a knob, which can include a knob body 736 and a knob cover 738. The instrument can also be configured to be vented or sealed using movement of the knob body 736 and knob cover 738, which causes movement of other components of the instrument relative to one another to open or close one or more passages, as described herein. The instrument 700 can include a spring 750, which can be disposed internally within the instrument. In some embodiments, a proximal end of the spring 750 may push against a tensioner 752 (or other component that remains stationary with and/or is held by the proximal housing 732), and a distal end of the spring 750 may push against a manifold body 746 (or other component that axially translates toward the proximal housing 732 in response to an operator pushing on the knob).

The spring 750 (e.g., similar to the spring 950) can be configured to proximally bias the knob body 736 in a position that prevents its rotation relative to the proximal housing 732 of the instrument 700. The knob body 736 may be configured to distally translate relative to the proximal housing 732 in response to a force (e.g., pushing force) being applied to the knob cover 738 (and therefore the knob body 736) that is sufficient to compress the spring 750. As such, the force exerted by the spring is configured to ensure that the knob (including the knob cover 738 and the knob body 736) is secured in the first configuration (e.g., venting configuration). When the knob body 736 is distally translated, it causes the manifold body 746 to distally translate, thereby compressing the spring between the manifold body 746 and the tensioner 752. Subsequently, the knob cover 738 (and therefore the knob body 736) can be rotated relative to the proximal housing 732. Rotation of the knob body 736 relative to the proximal housing 732 can couple or lock the instrument 700 to an instrument interface of a surgical robotic system, as described herein.

Figure 14A:
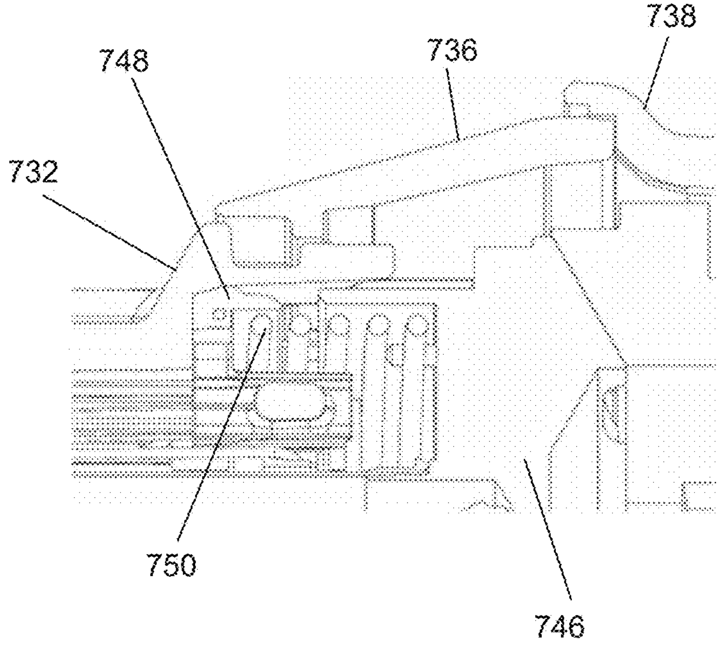
FIG. 14A depicts a close-up, cross-sectional side view of a portion of the surgical instrument of FIG. 7 in a first configuration, according to embodiments.
Figure 14B:
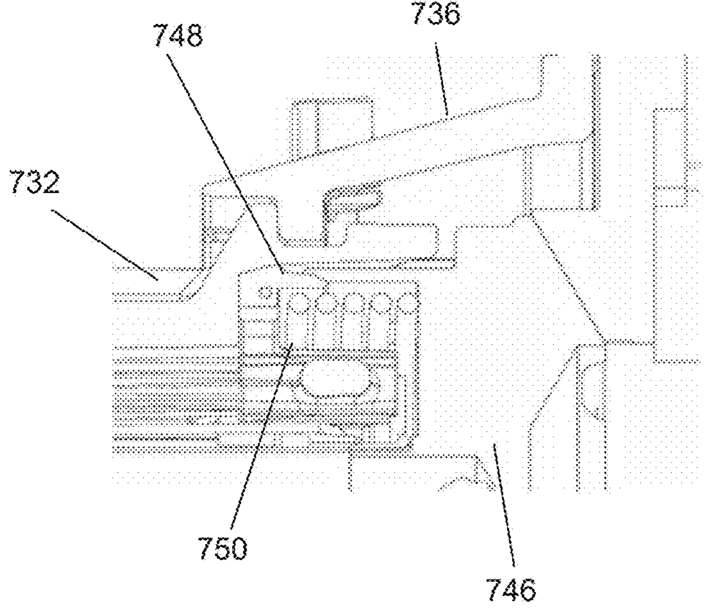
FIG. 14B depicts a close-up, cross-sectional side view of a portion of the surgical instrument of FIG. 7 in a second configuration, according to embodiments.

FIG. 9 depicts the instrument 700 after the knob body 736 and the knob cover 738 have been pushed distally (e.g., toward the proximal housing 732) and rotated. In this position, one or more sealing elements can be configured to seal an interior space of the instrument 700, e.g., to prevent fluid (e.g., a bodily fluid) from escaping the interior space during a surgical operation. In some embodiments, one or more manifold structures can be used to seal the interior space of the instrument. For example, a first sealing engagement is formed between a manifold seal 748 (e.g., a first sealing element) and the manifold body 746 (e.g., a second sealing element). FIGS. 14A and 14B show closer, more detailed views of this engagement between the manifold body 746 and the manifold seal 748. FIG. 14A depicts a detailed cross-sectional side view of the instrument 900 in a first configuration (e.g., venting configuration). FIG. 14B depicts a detailed cross-sectional side view of the instrument 900 in a second configuration (e.g., in-use configuration). In the first configuration, a gap or opening between the manifold seal 748 and the manifold body 746 provides access for fluid (e.g., liquid and/or gas) to enter or exit from an interior space of the instrument 700. In this configuration, the opening between the manifold seal 748 and the manifold body 746 allows liquid and gas to leave or enter the instrument during sterilization and/or reprocessing. In the second configuration, this opening is closed, thereby preventing liquid and/or gas from entering and/or exiting the interior space of the instrument 700.

Figure 15:
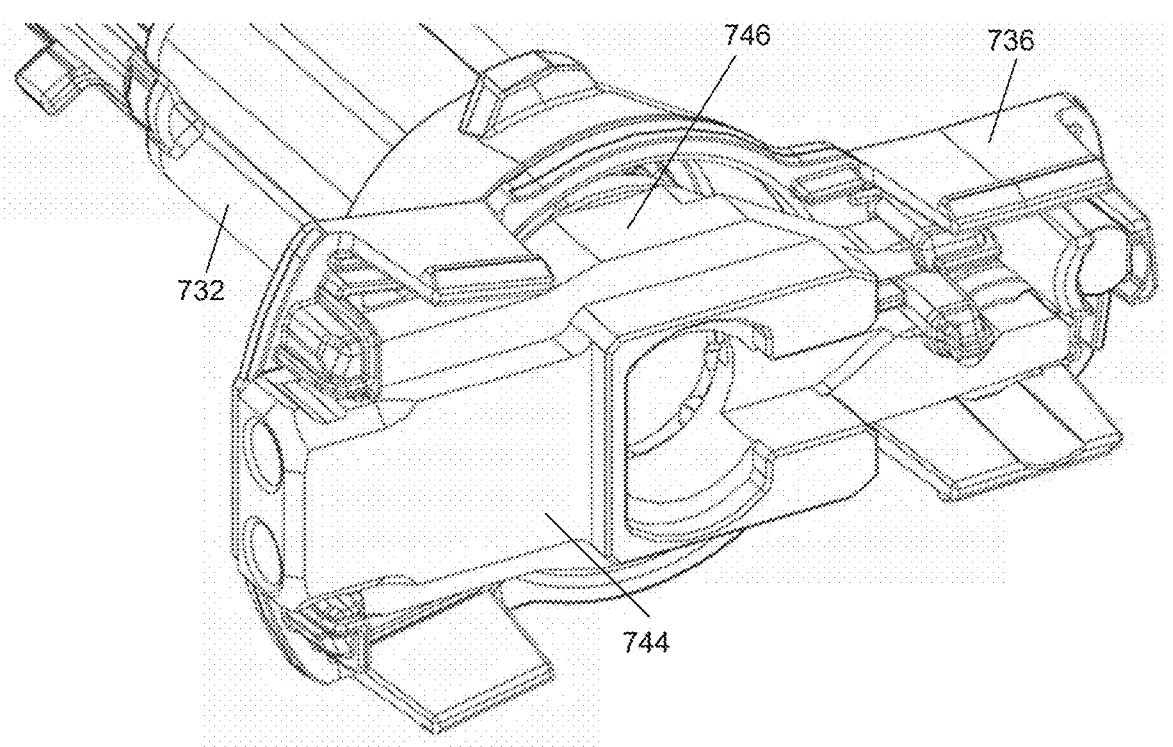
FIG. 15 depicts a perspective view of the surgical instrument of FIG. 7, with certain components removed to show underlying components, according to embodiments.
Figure 16:
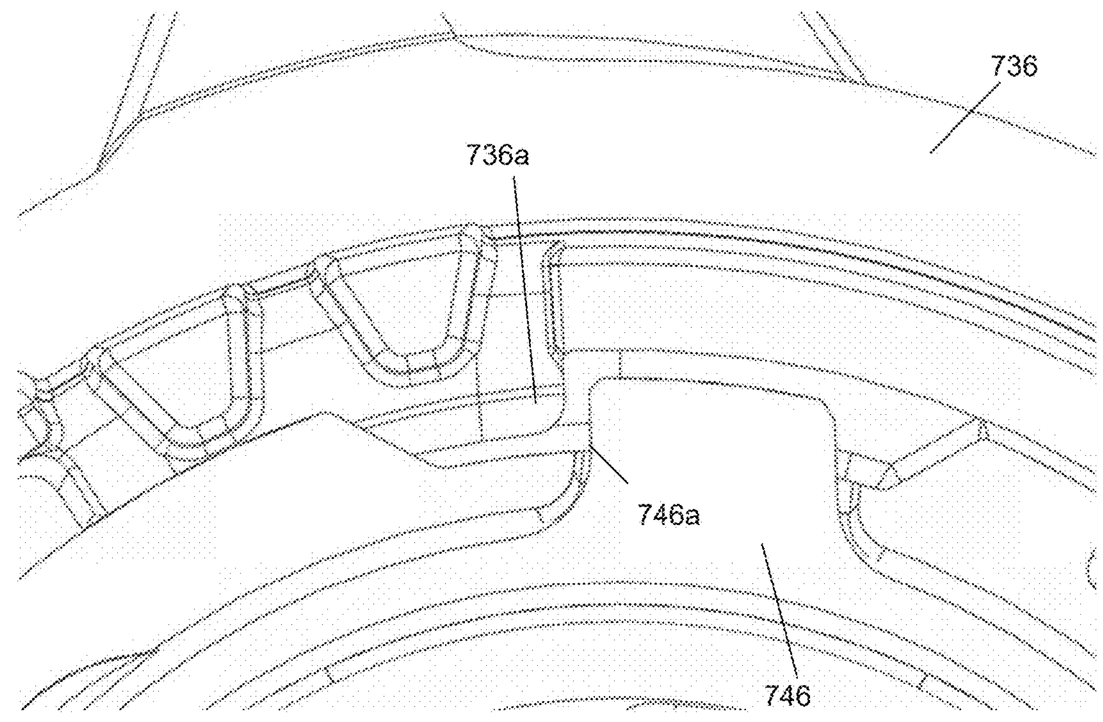
FIG. 16 depicts a close-up view of a portion of the surgical instrument of FIG. 7, according to embodiments.
Figure 17A:
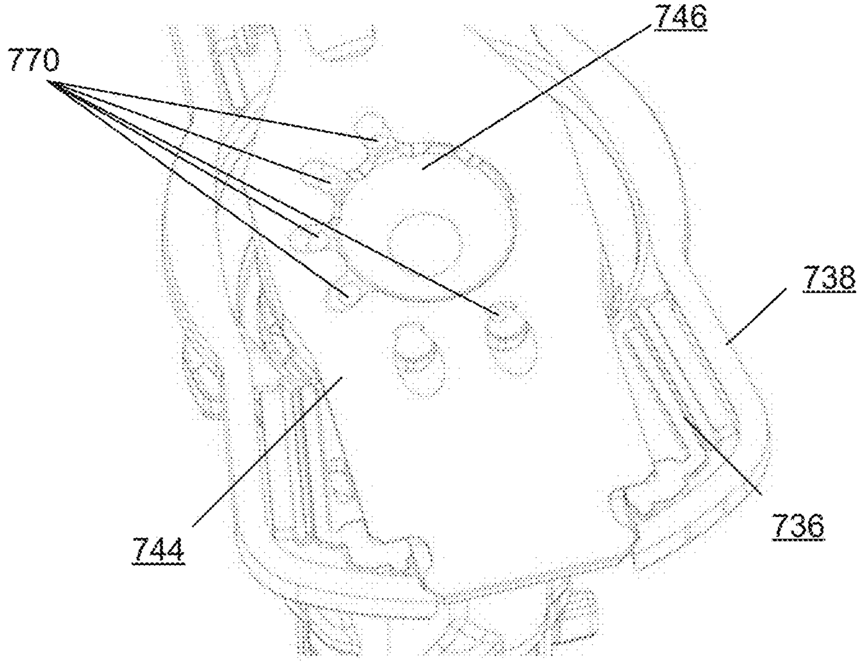
FIG. 17A depicts a perspective cutaway view of the surgical instrument of FIG. 7 in a first configuration, according to embodiments.
Figure 17B:
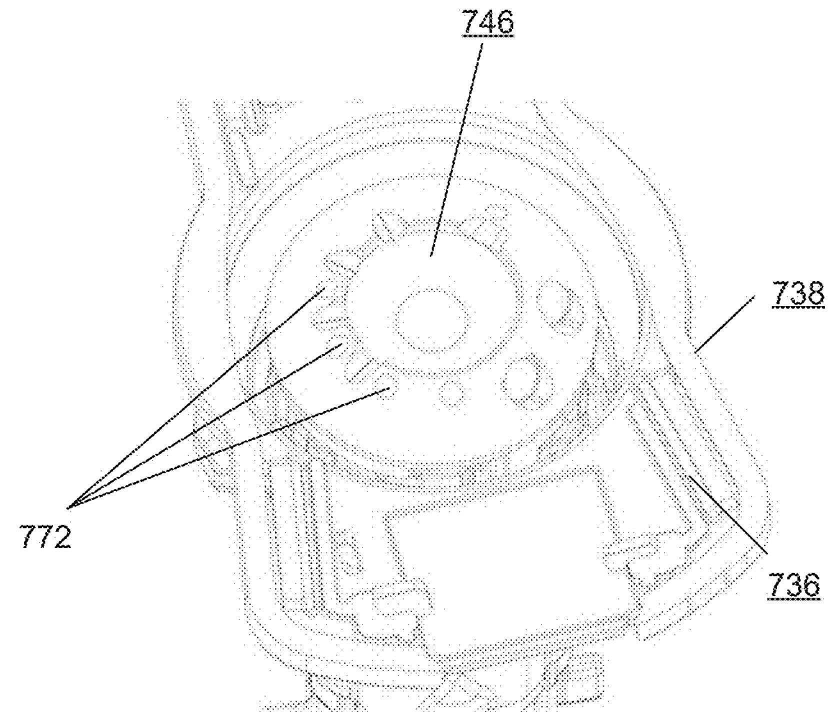
FIG. 17B depicts a perspective cutaway view of the surgical instrument of FIG. 7 in a second configuration, according to embodiments.

In some embodiments, venting and sealing of the instrument 700 can also be provided through the manifold body 746 (e.g., a second sealing element) and one or more manifold ports 744 (e.g., a third sealing element). While these components are referred to herein as a second and a third sealing element, it can be appreciated that such naming is merely for illustrative purposes and that either can be referred to as a first sealing element and/or a second sealing element. These components are shown in the cross-sectional view of FIG. 9, and are shown in greater detail in FIGS. 15, 17A and 17B. FIG. 15 depicts a perspective cutaway view of the instrument 700, including the one or more manifold ports 744 and the manifold body 746. The manifold body 746 can include one or more channels or passages, which can be aligned with the one or more manifold ports 744 to allow for venting or passage of fluids in and/or out of the interior space of the instrument 700. FIG. 17A depicts the manifold ports 744 and the manifold body 746 when the instrument 700 is in the first configuration (e.g., venting configuration), and FIG. 17B depicts the manifold ports 744 and the manifold body 746 when the instrument 700 is in the second configuration (e.g., in-use configuration). When the one or more manifold ports 744 and the manifold body 746 are in the first configuration, the one or more manifold ports 744 and the one or more channels of the manifold body 746 are aligned and configured to allow passage 770 of a cleaning fluid into the interior space and other interior regions of the instrument, e.g., to facilitate cleaning and/or sterilization of internal components of the instrument. The internal components of the instrument 700 may include elements such as, for example, cables 722, spring 750, tensioner 752, and/or other components not exposed to the external environment (e.g., not visible from an external view of the instrument 700). As shown in FIG. 17B, when the one or more manifold ports 744 and the manifold body 746 are in the second configuration, the one or more manifold ports 744 and one or more channels of the manifold body 746 are misaligned, and therefore the channels are blocked 772. In this configuration, the interior space of the apparatus is sealed, e.g., to prevent fluids from leaving the interior space of the instrument 700. The manifold ports 744 may be configured to move relative to the manifold body 746 to form a fluid-tight seal that prevents fluids from leaving an interior space and other interior regions of the instrument 700. For example, the manifold ports 744 can be configured to rotate relative to the manifold body 746 in a first direction (e.g., clockwise) to transition from the first configuration to the second configuration to seal the interior space of the instrument 700. The interior space of the instrument can include portions of the instrument 700 not exposed to an external environment (e.g., not visible from an external view of the instrument). Additionally, the manifold ports 744 can be rotated back in a second direction (e.g., counter-clockwise) to transition from the second configuration back to the first configuration.

As described above, two types of fluid may enter the interior space and other interior regions of the instrument. The first type of fluid may include one or more of bodily fluid, blood, saline, water, etc. and the second type of fluid may include cleaning fluid (e.g., liquid, gas). During a surgical procedure, if the instrument is not properly sealed, then fluids may enter the interior of the instrument 700 and flow toward the proximal head. If fluids exit through the proximal head, they may penetrate the surgical robotic system's instrument interface (including electronic components) and damage it. To prevent fluids from entering the surgical robotic system, fluids present inside the interior of the instrument can be sealed from escaping when the instrument 700 is in the second (in-use) configuration, as shown in FIG. 17B. Prior to or after the surgery, the instrument may undergo a cleaning process to facilitate use and/or reuse. For example, an interior of the instrument may be cleaned when the first manifold structure and the second manifold structure are in the first (venting) configuration, as shown in FIG. 17A. When the interior of the instrument is accessible, the cleaning fluid may be injected or otherwise delivered into the interior of the instrument through ports and channels, thereby flushing debris, fluids, and/or other contaminants out of the interior space of the instrument.

In some embodiments, the manifold ports 744 may be configured to rotate relative to the manifold body 746 in response to the knob body 736 being rotated relative to the proximal housing 732. This configuration can provide a simple mechanism for changing from the first configuration (e.g., venting configuration) to the second configuration (e.g., the in-use configuration). As described herein, axial translation and rotation of the knob body 736 relative to the proximal housing 732 (e.g., from a first position to a second position, similar to that shown in FIGS. 24 and 25) can cause the instrument 700 (in particular, the proximal head of the instrument) to lock to an instrument interface of a surgical robotic system. Subsequent to locking the instrument 700 to the instrument interface, the instrument 700 can be used in a surgical procedure. The knob body 736 can then be rotated back (e.g., from the second position back to the first position) to unlock the instrument 700 from the instrument interface and to allow the instrument 700 to be disengaged or removed from the instrument interface of the surgical robotic system. In some embodiments, before the knob body 736 can be rotated back, the knob body 736 may need to be axially translated distally (e.g., pushed toward the proximal housing 732) to unlock the knob body 736 for rotation relative to the proximal housing 732. This configuration can permit secure unlocking of the instrument from the instrument interface.

Extending from this description of the knob body 736 and the sealing elements described above (e.g., the manifold seal 748, manifold body 746, and the manifold ports 744), in some embodiments, the knob body 736 may be distally translated and rotated relative to the proximal housing 732 to lock the instrument 700 (in particular, the proximal head of the instrument) to an instrument interface of a surgical robotic system and to cause one or more sealing elements to form fluid-tight seals that prevent fluids from exiting the internal space of the instrument. The knob body 746 can subsequently be rotated back relative to the proximal housing 732 to unlock the instrument 700 from the instrument interface and to cause the one or more sealing elements to unseal, e.g., opening one or more passages that enable delivery of fluid (e.g., cleaning fluids) into the interior space of the instrument to sterilize the instrument and its interior components.

In some embodiments, the push-to-turn feature of the instrument 700 can be implemented via an interface between the proximal housing 732 and the knob body 736. The proximal housing 732 can include a gap that allows the knob body 736 to be assembled into the proximal housing 732. The knob body 736 may have a plurality of extensions 736*a* (e.g., male bayonet features), which interface with corresponding recesses 732*a* (e.g., female bayonet features) on an outer surface of the proximal housing 732. During rotation of the knob body 736 relative to the proximal housing, audible and/or haptic feedback may be provided to the user, e.g., to provide confirmation of the instrument 700 being transitioned from a first configuration (e.g., a venting configuration) to a second configuration (e.g., in-use configuration), or from the second configuration to the first configuration. For example, the audible and/or haptic feedback may take the form of a click feature where a set of one or more flexible arms (e.g., extensions) of the knob body 736 is configured to click into corresponding grooves (e.g., recesses) of the proximal housing 732 in each configuration. These features can help prevent accidental rotation of the knob and removal of the instrument during use. Therefore, less interference is required between external bayonet features on the knob body 736 and the sterile interface, allowing for higher tolerances. The audible and/or haptic feedback can improve the usability of the instrument, e.g., by helping the operator know without doubt whether the instrument has been properly locked to the surgical robotic system and placed into a sealed configuration.

Figure 10:
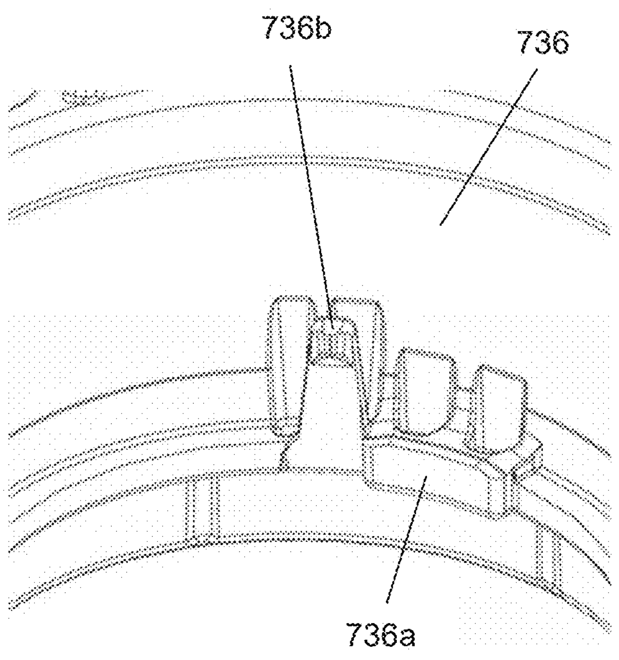
FIG. 10 depicts a detailed perspective view of a knob of the surgical instrument of FIG. 7, according to embodiments.
Figure 11:
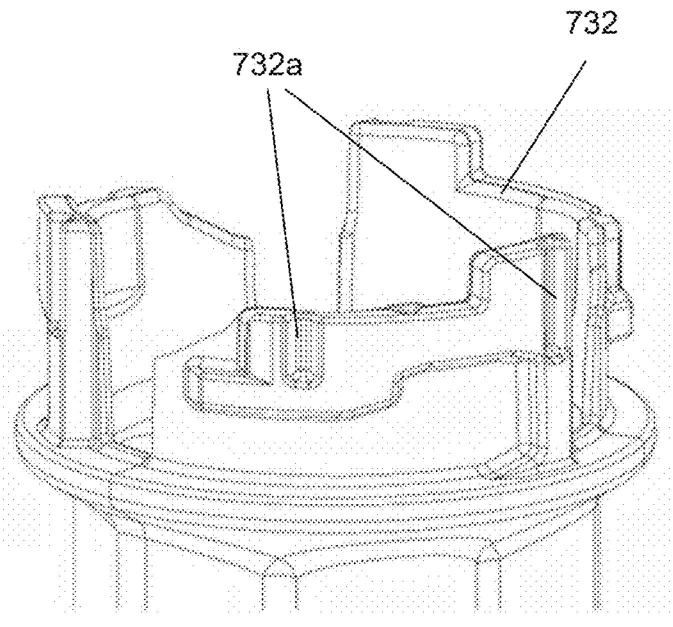
FIG. 11 depicts a detailed perspective view of a proximal housing of the surgical instrument of FIG. 7, according to embodiments.

FIG. 10 provides a detailed perspective view of a knob body 736 of the instrument 700, according to embodiments. The knob body 736 may include one or more arms configured to interface with one of more corresponding features 732*a* (e.g., recesses) disposed on the proximal housing 732, e.g., to provide audible and/or haptic feedback to a user when the knob body 736 is distally translated and subsequently rotated relative to the housing 732. The arms may include one or more extensions 736*a* (e.g., internal male bayonet features) and click elements 736*b* adjacent thereto. FIG. 11 depicts a perspective view of the proximal housing 732 of the instrument 700, including the plurality of recesses 732*a* (e.g., female bayonet features) configured to interface with the corresponding arms of the knob body 736.

When the instrument 700 is unlocked (e.g., in the first configuration, venting position), the spring 750 can be configured to apply a load to the extensions 736*a* of the knob body 736, to retain the extensions 736*a* in the recess 732*a* of the proximal housing 732. This prevents the knob body 736 from rotating relative to the proximal housing 732. The knob body 736 and proximal housing 732 may be configured to maintain its form (e.g., not significantly creep or deform, have sufficient thermal stability) during reprocessing at elevated temperatures. During use, the load applied to the engagement elements 740 may be transmitted to the proximal housing 732, e.g., via the cables 722, shaft (e.g., shaft 620), and distal housing 734. This axial load may be held by a shoulder 732*b* on the knob body 736, and subsequently transmitted to external extensions (e.g., external bayonet features) of the knob body 736, which are held in the sterile interface of the surgical robotic system. This axial load can be as high as the total load applied to three pairs of engagement elements 740, e.g., up to 60 N. The proximal housing 732 and the knob body 736 can be designed to remain in fixed relation to one another during use, e.g., up to forces as high as 60 N.

FIG. 12 depicts a knob travel path 760 with respect to the proximal housing 732. This knob travel path 760 is the path that is taken by portions of the knob body 736 (in particular, the extensions 736*a* and the click element 736*b*) during a push-to-turn operation. FIG. 13A depicts a side cutaway view of the instrument 700 in the first configuration (e.g., venting configuration), including the proximal housing 732 and the knob body 736 in a first position relative to one another. In the first position, the extensions 736*a* and the click element 736*b* of the knob body 736 are disposed in a first recess 732*a* of the proximal housing 732, with the extensions 736*a* of the knob body 736 are disengaged from the shoulder. The extensions 736*a* can be biased (e.g., by spring 750) to remain in the recess 732*a*, e.g., to prevent the knob body 736 from easily rotating relative to the proximal housing 732. A user can then perform a push-to-turn operation, whereby the user first pushes to the knob cover 738 to axially translate the knob cover 738 and knob body 736, such that the biasing force of the spring 750 is overcome, and then rotates the knob cover 738 to rotate the knob cover 738 and knob body 736 to move the knob body 736 to a second position relative to the proximal housing 732. FIG. 13B depicts a side cutaway view of an instrument 700 in this second position (e.g., an in-use configuration). In this second position, the extensions 736*a* and the click element 736*b* of the knob body 736 are disposed in a second recess 732*a* of the proximal housing 732, with the extensions 736*a* engaged with the shoulder 732*b*.

In some embodiments, the manifold body 746 can be configured to prevent over-rotation of the knob body 736 relative to the proximal housing 732. In particular, the manifold body 746 can include a stopping surface 746*a* that is configured to engage with the extensions 736*a* of the knob body 736 to prevent rotation of the knob body 736 relative to the proximal housing 732 beyond a certain predefined point (e.g., beyond the in-use position or configuration). As such, the manifold body 746 can act as an end-stop against over-rotation of the knob body 736. This can prevent accidental disassembly or decoupling of the knob body 736 from the proximal housing 732. This design of the manifold body 746 improves the manufacturability and/or assembly of the instrument.

The push-to-turn operation as described herein combines an axial translation (e.g., compression against the spring 750) with rotational movement to engage the external bayonet features on the knob body 736 into the sterile interface of a surgical robotic system, while also sealing the interior space of the instrument 700. In some embodiments, the axial movement between a first configuration and a second configuration may be between about 1 mm and about 10 mm, between about 2 mm and about 8 mm, between about 2 mm and about 6 mm, between about 2 mm and about 4 mm, between about 2 mm and about 3 mm, including all ranges and sub-ranges therebetween. In the first configuration, the instrument can be ready for insertion to the instrument interface of the surgical robotic system and/or removable from the instrument interface. In the first configuration, the instrument may also provide passages for delivery of fluids, thereby facilitating reprocessing and sterilization, including, for example, the use of steam in an autoclave. In the second configuration, the instrument may be mechanically coupled to a sterile interface and sealed to form a fluid-tight barrier, e.g., to prevent escape of fluids that enter the interior space of the instrument during a surgical procedure.

Single-Use Instrument

FIGS. 18-21 depict an example of an instrument 800 of a surgical robotic system, according to embodiments. The instrument 800 can be a single-use instrument, e.g., an instrument that is used during a single surgical procedure and discarded. The instrument 800 can be configured to be sterilized prior to its use, and then sealed during use to prevent escape of fluids (e.g., bodily fluids).

Figure 18:
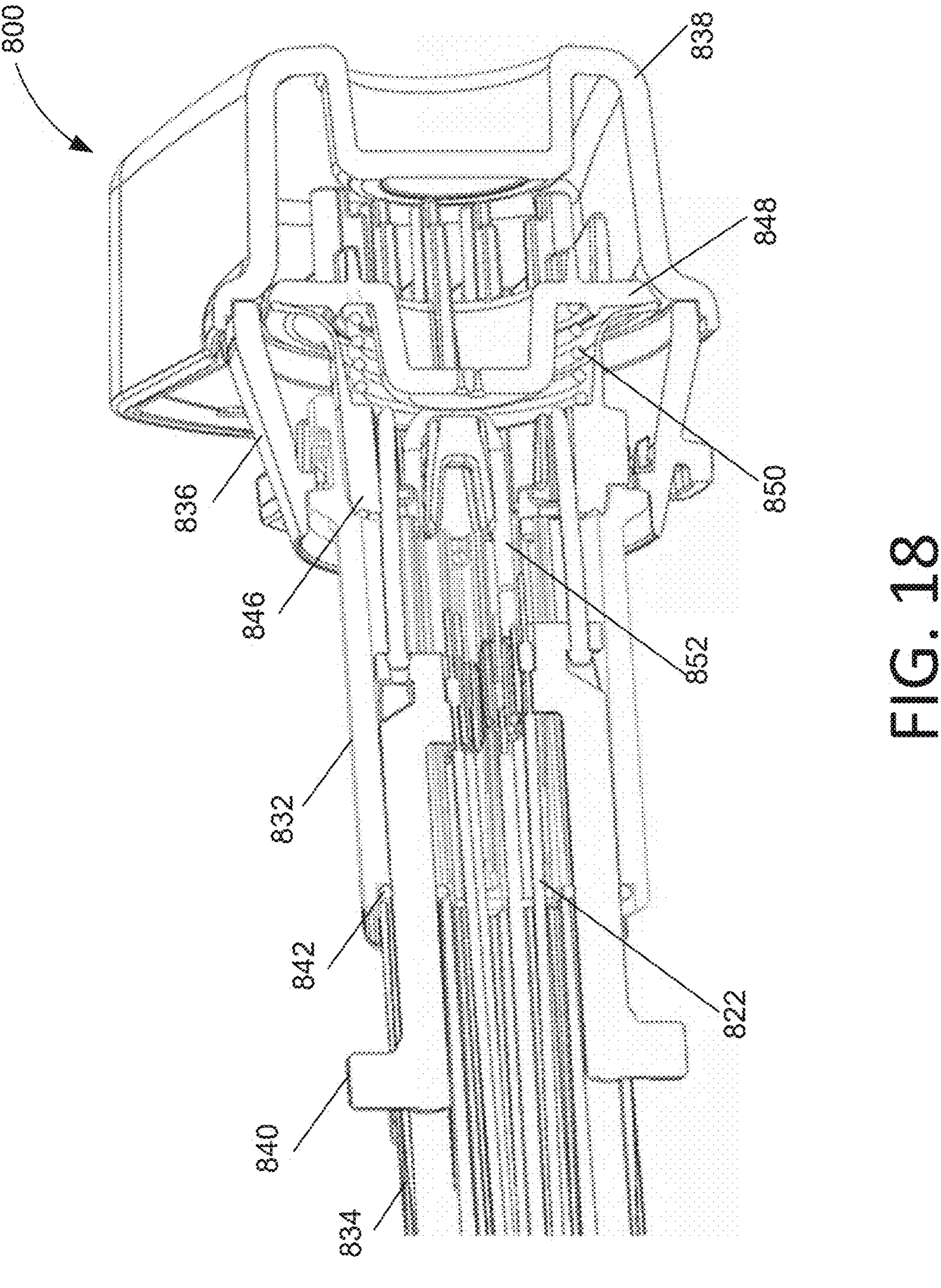
FIG. 18 depicts a cross-sectional view of a proximal end of a surgical instrument of a surgical robotic system, according to embodiments.

FIG. 18 depicts a cross-sectional side view of a proximal end of the instrument 800. The instrument 800 can be functionally and/or structurally similar to other instruments described herein, including the instruments 600 and 700, and therefore can include similar components as such instruments. For example, the instrument 800 may include a shaft (e.g., similar to shaft 620) including a proximal end and a distal end. The shaft may define a lumen extending between the proximal end and the distal end. An end effector (e.g., end effector 610) may be disposed at the distal end of the shaft. A proximal head (e.g., proximal head 630) may be disposed at the proximal end of the shaft. As shown in FIG. 18, the proximal head may include one or more housings (e.g., a proximal housing 832 and a distal housing 834) defining an internal space or lumen configured to house a plurality of engagement elements 840, and a knob disposed proximal of the housings. The knob may comprise a knob body 836 and a knob cover 838 coupled to and proximal to the knob body 836. Each engagement element of the plurality of engagement elements 840 may be coupled to the end effector via cables 822 (e.g., force transmitting elements) disposed within the lumen.

Similar to other instruments described herein, the instrument 800 may selectively form a fluid-seal using the knob (including the knob cover 838 and a knob body 836). The instrument 800 may include a spring 850, which can be configured to bias the knob body 836 into a position that prevents its rotation relative to a proximal housing 832. The spring 850 may be coupled between a tensioner 852 and a base cap 848. A distal portion of the spring 850 may push against the tensioner 852 and a proximal portion of the spring 850 may push against the base cap 848. The knob body 836 may be configured to distally translate relative to the proximal housing 832 in response to a force (e.g., pushing force) being applied to the knob body 836 that is sufficient to compress the spring 850. The knob body 836 may further be configured to be rotated (after being distally translated) relative to the proximal housing 832, e.g., to lock the instrument 800 to an instrument interface of a surgical robotic system and to seal an interior space of the instrument 800 so that fluids cannot exit therefrom.

As shown in the detailed cross-sectional side view of FIG. 18, a sealing unit 842 (e.g., structurally and/or functionally similar to sealing unit 742) may be disposed between the proximal housing 832 and the distal housing 834. The sealing unit 842 may be configured to form a fluid-tight seal with the plurality of engagement elements 840 to prevent fluids from leaving an interior space and other interior regions of the instrument 800. Each engagement element 840 may be disposed within a corresponding slot. The plurality of engagement elements 840 may be configured to extend through the sealing unit 842. The instrument 800 may include a plurality of slots disposed circumferentially around a longitudinal axis of the instrument 800. The instrument 800 may include a plurality of cables 822 (e.g., force transmitting elements) disposed within and extending through a lumen of the shaft. In some embodiments, each engagement element of the plurality of engagement elements 840 may be configured to translate relative to the proximal housing 832 and the distal housing 834 to actuate the end effector in at least one degree-of-freedom. In some embodiments, each engagement element of the plurality of engagement elements 840 may be coupled to one or more actuators of a surgical robotic system, and may be configured to be driven by an actuator of the one or more actuators to axially translate relative to the sealing unit 842 to move the end effector.

In some embodiments, the instrument 800 can include a base structure or cap 842 (e.g., a first sealing element) and a base seal 846 (e.g., a second sealing element). As noted previously, while components described with respect to instruments of the present disclosure are referred to using "first," "second," and so on, it can be appreciated that any of these components can be referred to using a different designator (e.g., second as opposed to first), without departing from the scope of the present disclosure. The base seal 846 can include a proximally facing surface that interacts with a distally facing surface of the base structure 842. The base structure 842 may be configured to be axially translated toward the base seal 846 such that the base seal 846 and the base structure 842 form a fluid-tight seal that is configured to prevent fluids from leaving an interior space and other interior regions of the apparatus, in response to the knob body 836 being distally translated relative to the housing 832. In some embodiments, the base seal 846 may be configured to deform against the distally facing surface of the base structure 842 to form the fluid-tight seal. The knob body 836 may be configured to be distally translated and/or rotated relative to the proximal housing 832 to lock the proximal head to an instrument interface of a surgical robotic system and to cause the base structure 842 to move relative to the base seal 846 to form the fluid-tight seal. Unlike the sealing elements described with respect to the instrument 700, the base seal 846 may provide sealing of the interior space of the instrument 800 but not have the durability to withstand repeated reprocessing at elevated temperatures. The base seal 846 and the base structure 842 can be configured to provide sealing without increasing stress to other components of the instrument (e.g., other plastic parts of the instrument, such as the knob and/or housing(s)) nor the force needed to switch to the in-use or sealed configuration.

Figure 21:
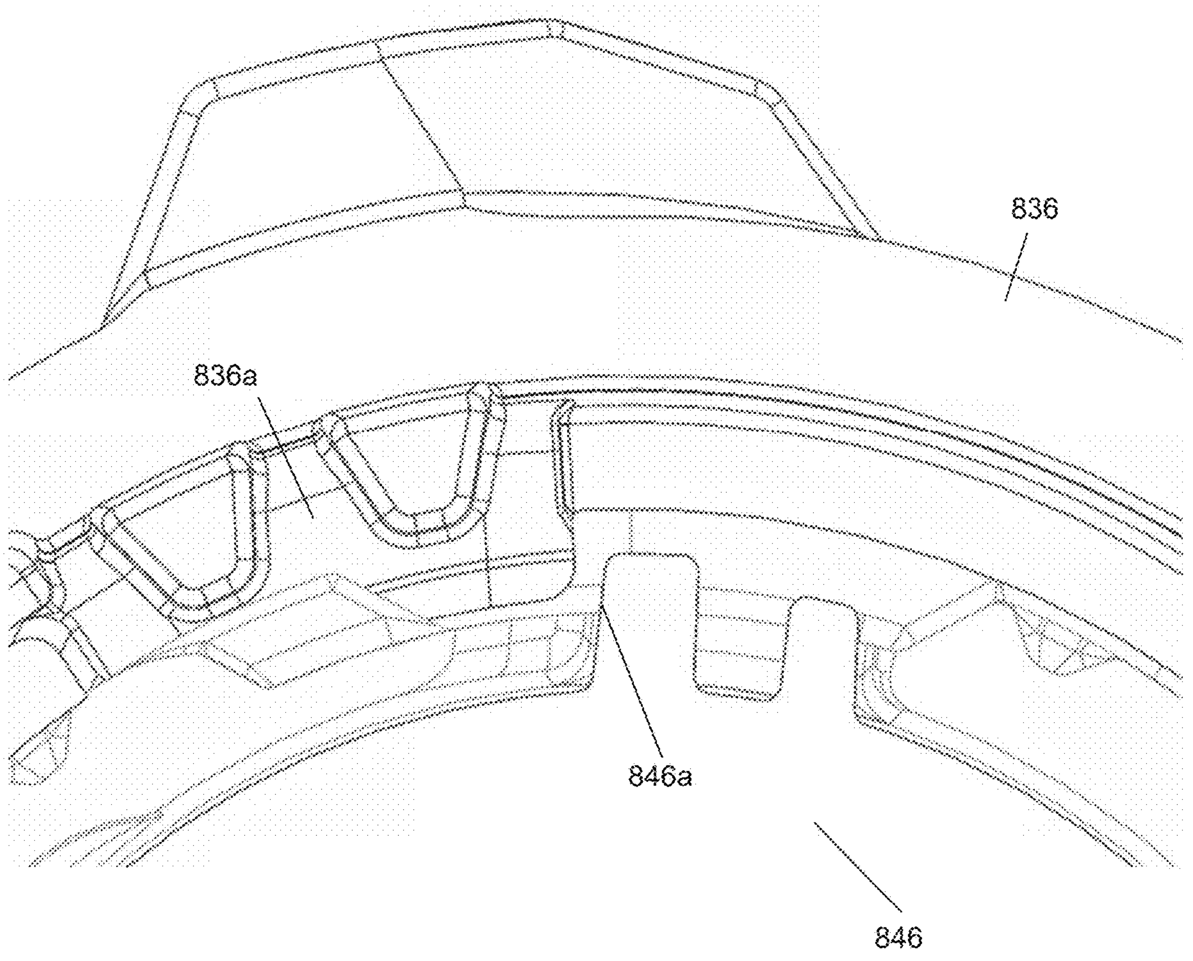
FIG. 21 depicts a close-up view of a portion of the surgical instrument of FIG. 18, according to embodiments.

In some embodiments, the seal 846 may include a stopping surface **846*a* configured to block the knob body 836 from rotating beyond a predefined position (e.g., an in-use configuration) to prevent separation of the knob body 836 from the housing 832. In doing so, the base seal 846 may be configured to prevent disassembly by functioning as an end-stop against a knob body to stop rotation beyond the in-use orientation. FIG. 21 depicts a front cross-sectional view of the instrument 800 including the base seal 846 with the stopping surface 846*a* configured to block the knob body 836 from rotating beyond a predefined position to prevent separation of the knob body 836 from the proximal housing 832. This design of the base seal 846** improves the manufacturability and/or assembly of the instrument.

Figure 19A:
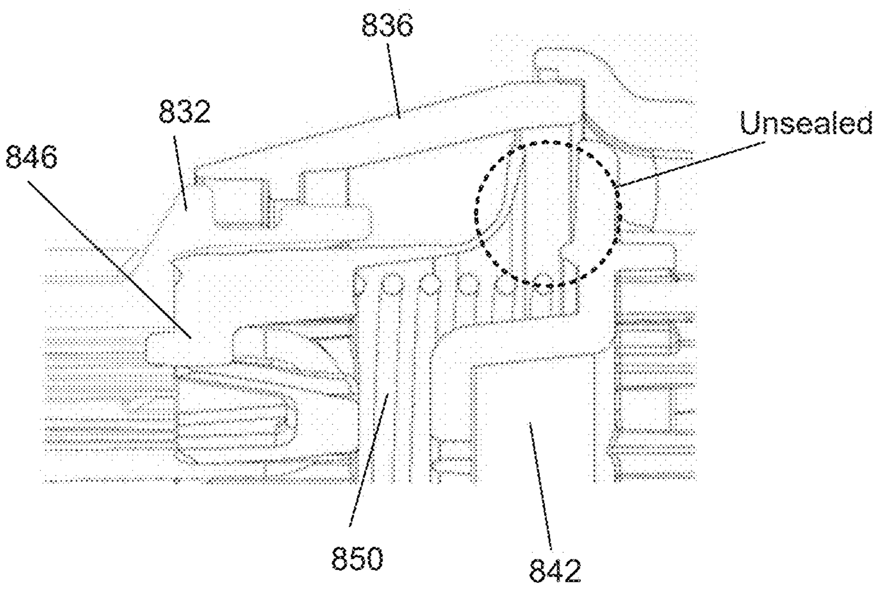
FIG. 19A depicts a close-up, cross-sectional view of a portion of the surgical instrument of FIG. 18 in a first configuration, according to embodiments.
Figure 19B:
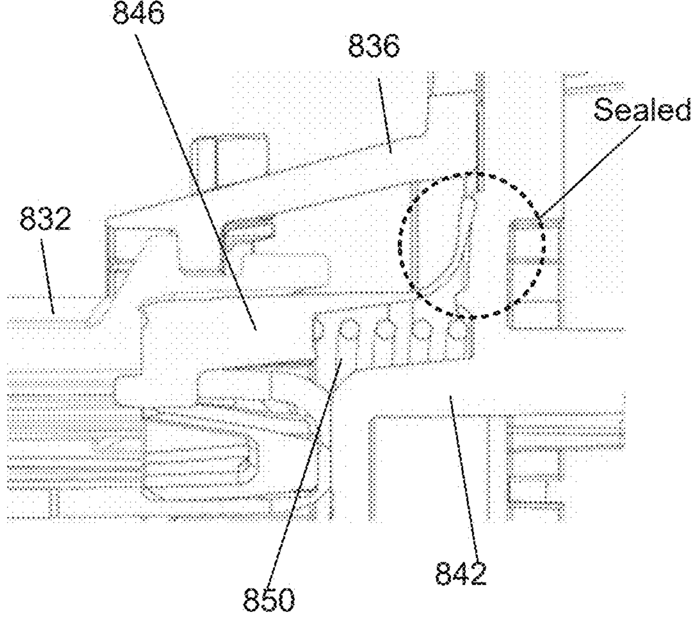
FIG. 19B depicts a close-up, cross-sectional view of a portion of the surgical instrument of FIG. 18 in a second configuration, according to embodiments.

FIG. 19A depicts a detailed cross-sectional side view of the instrument 800 in a first configuration (e.g., venting configuration). In the first configuration, a gap between the base seal 836 and base cap 848 provides access for fluid (e.g., liquid and/or gas) to enter an interior space of the instrument 800. For example, in the venting configuration, one or more passages may be opened to allow liquid and gas to leave or enter the instrument during sterilization, e.g., prior to initial use of the instrument. FIG. 19B depicts a detailed side cross-sectional view of the instrument 800 in a second configuration (e.g., in-use configuration) where the base seal 846 and base cap 848 form a fluid-tight seal. For example, the base seal 846 may be compressed against a sealing surface of the base cap 848. As described above, in response to the knob body 836 being distally translated relative to the housing 832, the base cap 848 is axially translated toward the base seal 846 such that the base seal 846 and the base cap 848 are in the in-use configuration, e.g., forming a fluid-tight seal that is configured to prevent fluids from leaving an interior space and other interior regions of the apparatus. The knob body 836 can subsequently be rotated in a first direction to lock the instrument to the instrument interface of the surgical robotic system. To remove the instrument, the knob body 836 can be rotated back in a second direction to unlock the instrument and to permit the knob body 836 to translate away from the base seal 846 to return to a venting or reprocessing configuration, and unsealing the interior space of the instrument. As such, this design can permit easy switching from a sealed or leak-tight configuration for use to an open or venting configuration for reprocessing.

Figure 20:
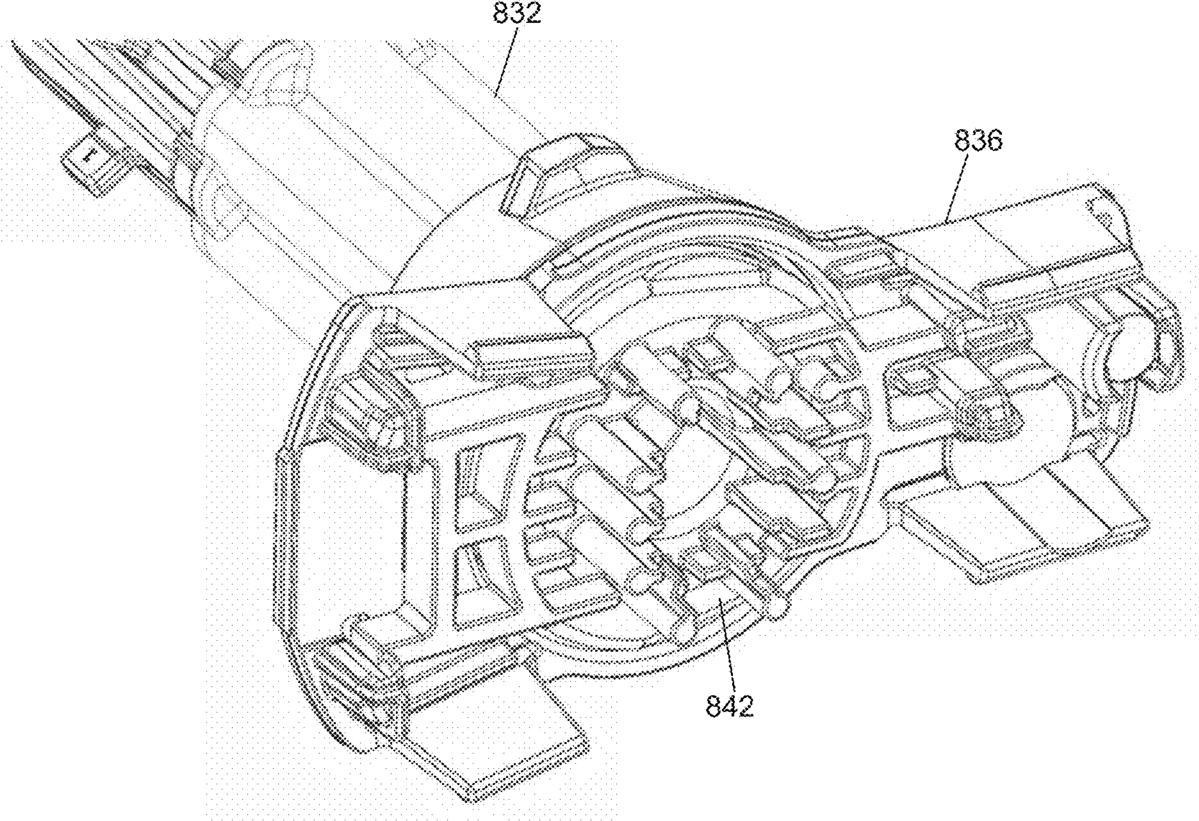
FIG. 20 depicts a perspective view of the surgical instrument of FIG. 18, with certain components removed to show underlying components, according to embodiments.

FIG. 20 depicts a perspective cutaway view of the instrument 800 including the proximal housing 832, the knob body 836, and the base cap 848, showing one or more openings through the base cap 848 that allow passage of fluid, when the instrument 800 is in the first configuration.

While not depicted and described again with respect to the instrument 800, it can be appreciated that the knob body 836 and the proximal housing 832 of the instrument 800 can move relative to one another, similar to that described with respect to the instrument 700. For example, the knob body 836 can include one or more extensions 836*a* (depicted in FIG. 21, and structurally and/or functionally similar to the one or more extensions 736*a*) and a click element (e.g., structurally and/or functionally similar to the click element 736*b*), and the proximal housing can include one or more recesses (e.g., structurally and/or functionally similar to the recesses 732*a*) that can receive the extensions 836*a* and the click element when they are in the first position (e.g., a venting position or configuration) and in the second position (e.g., an in-use position or configuration).

Alternative Designs

Figure 26:
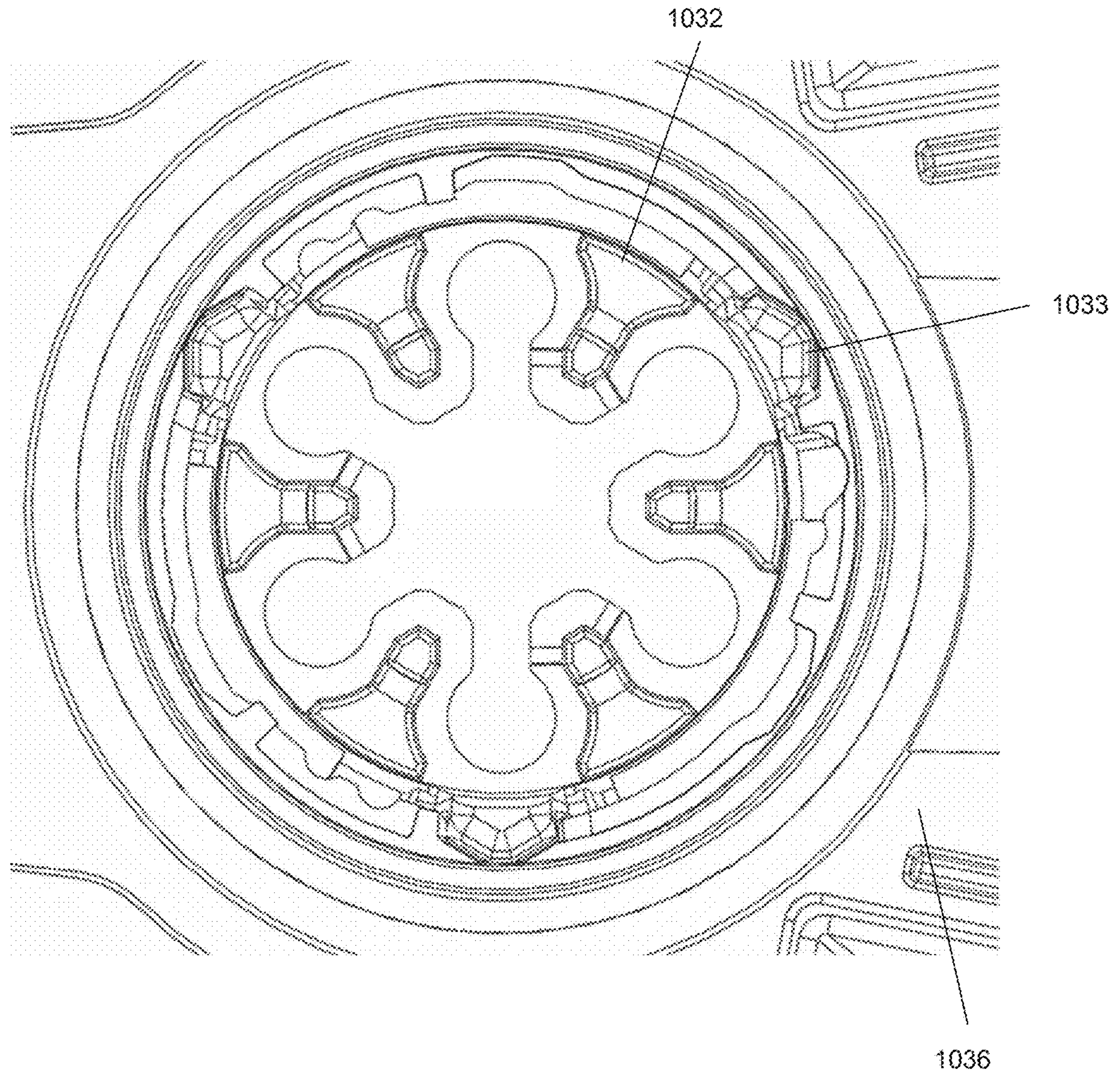
FIG. 26 depicts a cutaway view of a portion of a surgical instrument of a surgical robotic system, including a knob body having clipping features, according to embodiments.
Figure 27:
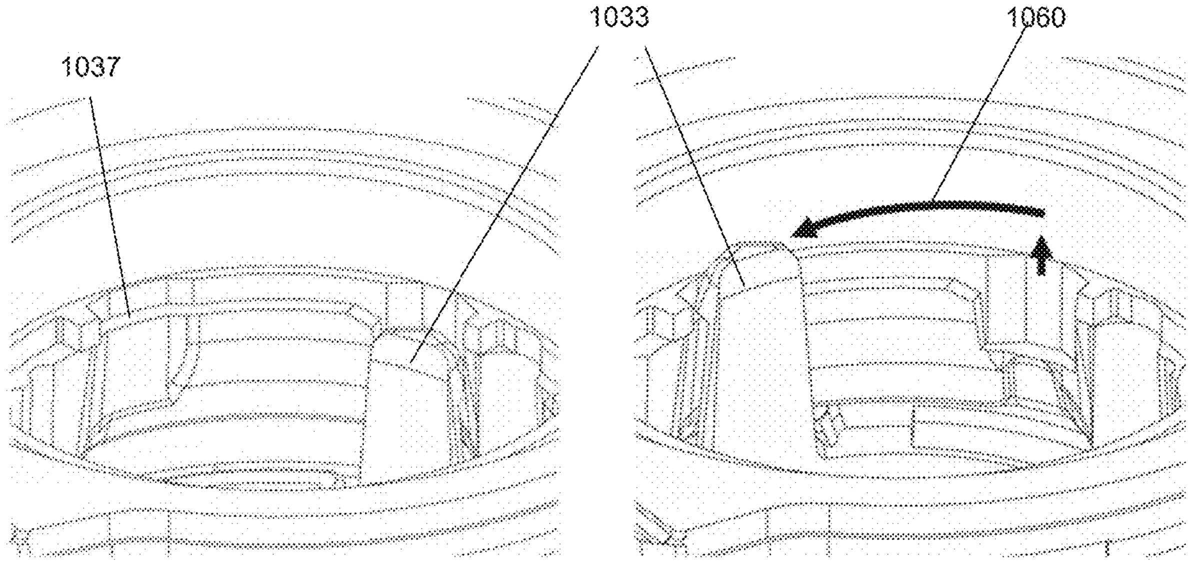
FIG. 27 depicts detailed views of the surgical instrument of FIG. 26, in two different configurations, according to embodiments.
Figure 28:
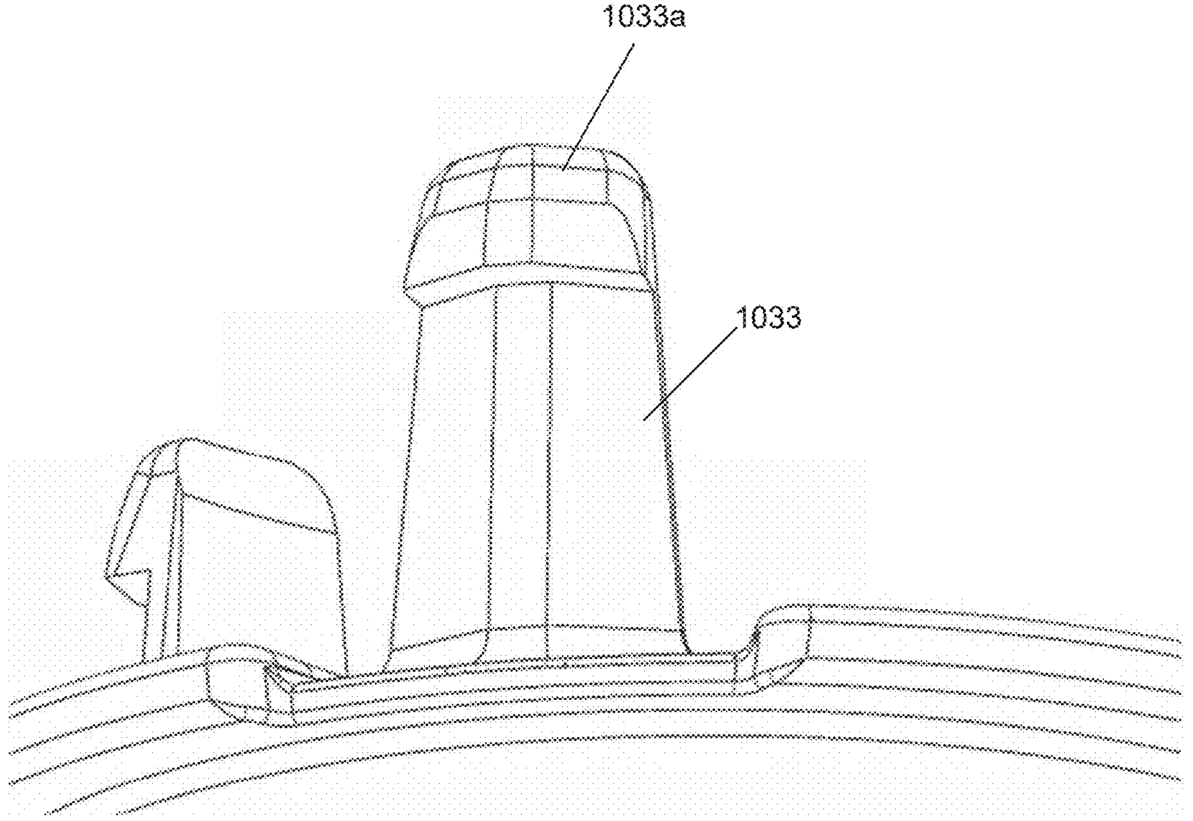
FIG. 28 depicts a detailed perspective view of the surgical instrument of FIG. 26, according to embodiments.

In some embodiments, a feature (e.g., click element) of a proximal housing of a surgical instrument may be configured to clip into a corresponding feature on the knob body 1036 of the surgical instrument. For example, FIG. 26 depicts a front cross-sectional view of a proximal housing 1032 including a click element 1033 at an end of a flexible clip, and a knob body 1036. Furthermore, FIG. 27 depicts a detailed cutaway perspective view of the click element 1033 configured to clip into a corresponding clipping feature 1037. A travel path 1060 of the click element 1033 to the clipping feature 1037 is depicted in FIG. 27. FIG. 28 depicts a detailed perspective view of the click element 1033 of the proximal housing having a clip 1033*a* that may be configured to couple (e.g., interface) with the clipping feature 1037.

Figure 29:
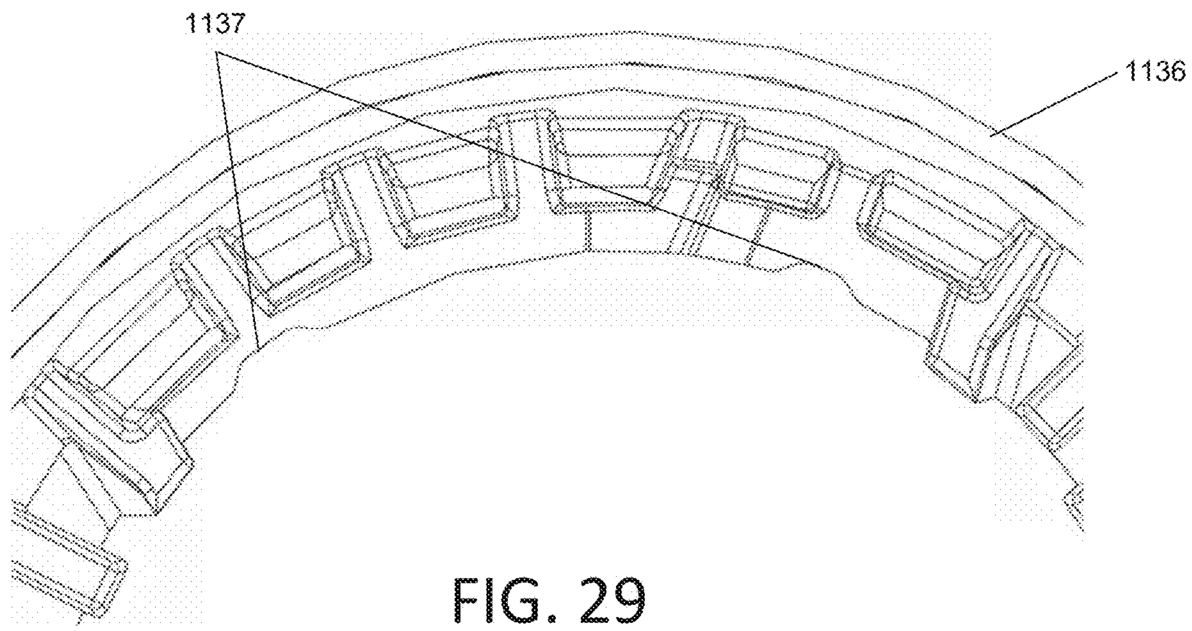
FIG. 29 depicts a detailed view of a knob body of a surgical instrument of a surgical robotic system, according to embodiments.
Figure 30:
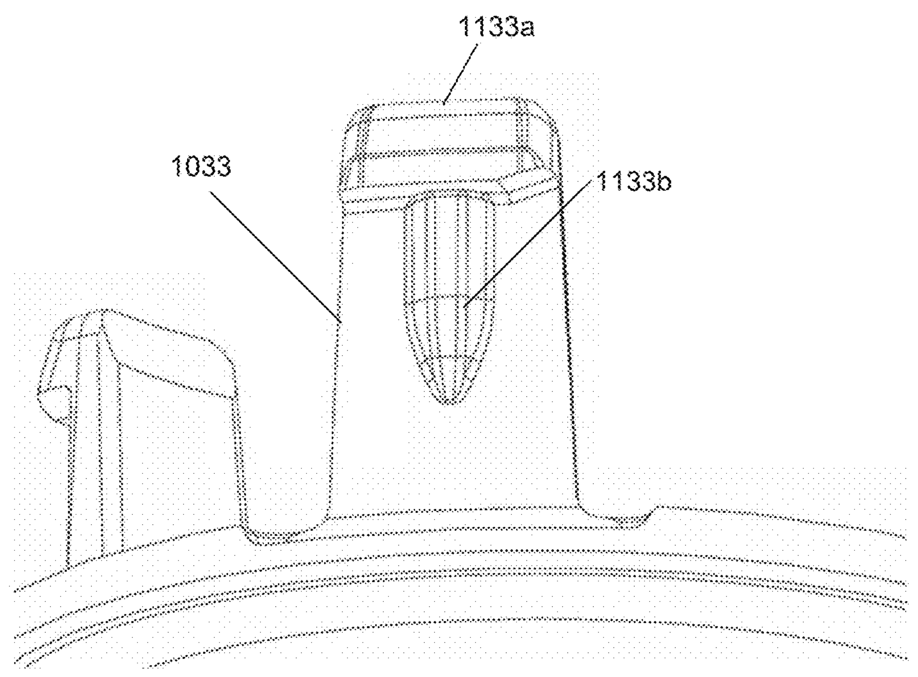
FIG. 30 depicts a detailed perspective view of a proximal housing of the surgical instrument of FIG. 29, according to embodiments.

In some variations, click elements may be provided on an arm of the clips. FIG. 29 depicts a detailed view of a knob body 1136 having a plurality of recesses 1137 configured to receive a corresponding click element 1033. For example, FIG. 30 depicts a detailed perspective view of a click element 1033 of a proximal housing including a clip 1133*a* and an extension 1133*b* protruding therefrom.

Figure 31:
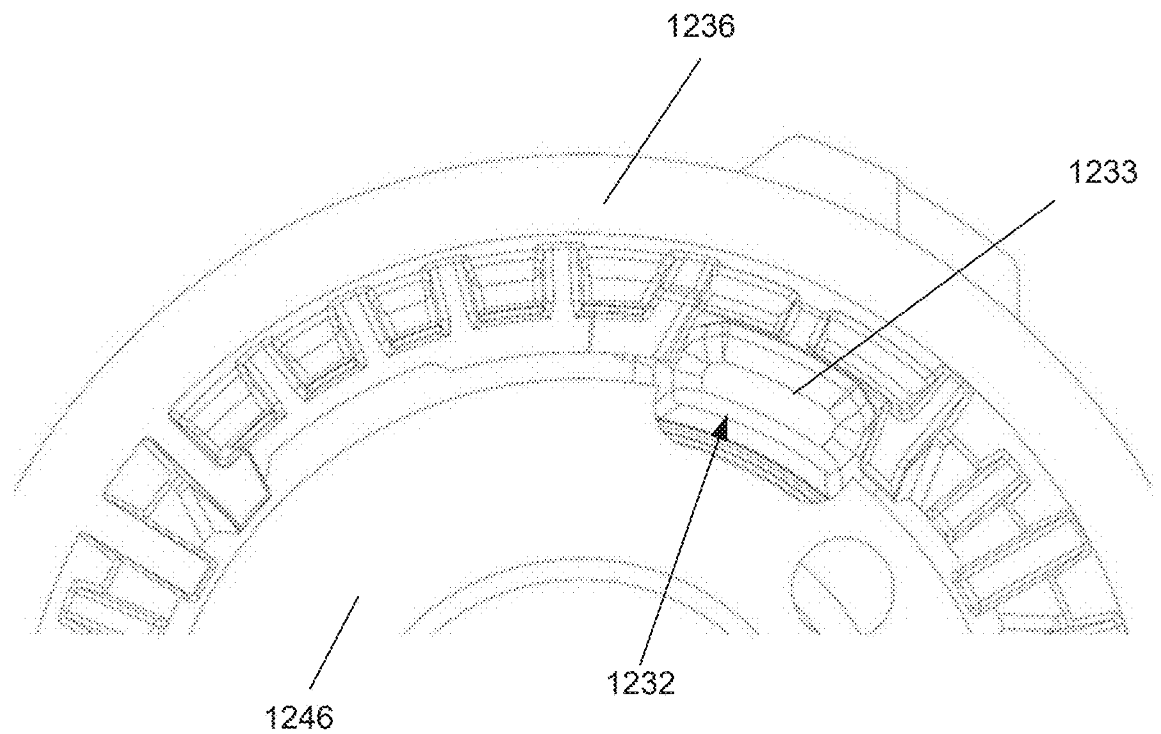
FIG. 31 depicts a detailed view of a proximal housing and a knob body of a surgical instrument of a surgical robotic system, according to embodiments.
Figure 32:
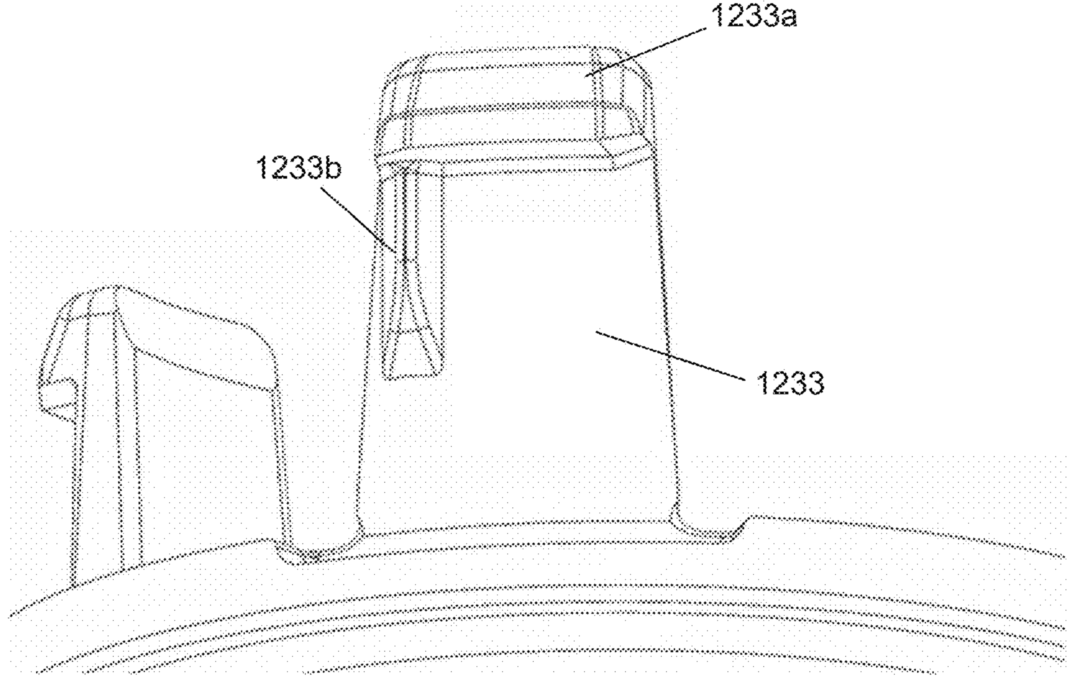
FIG. 32 depicts a detailed perspective view of a proximal housing of the surgical instrument of FIG. 31, according to embodiments.

FIG. 31 depicts detailed views of a proximal housing 1232, knob body 1236, and manifold body 1246. The proximal housing 1232 may include a click element 1233. FIG. 32 depicts a detailed perspective view of a proximal housing including a click element 1233 having a clip 1233*a* and an extension 1233*b* protruding therefrom.

Figure 33:
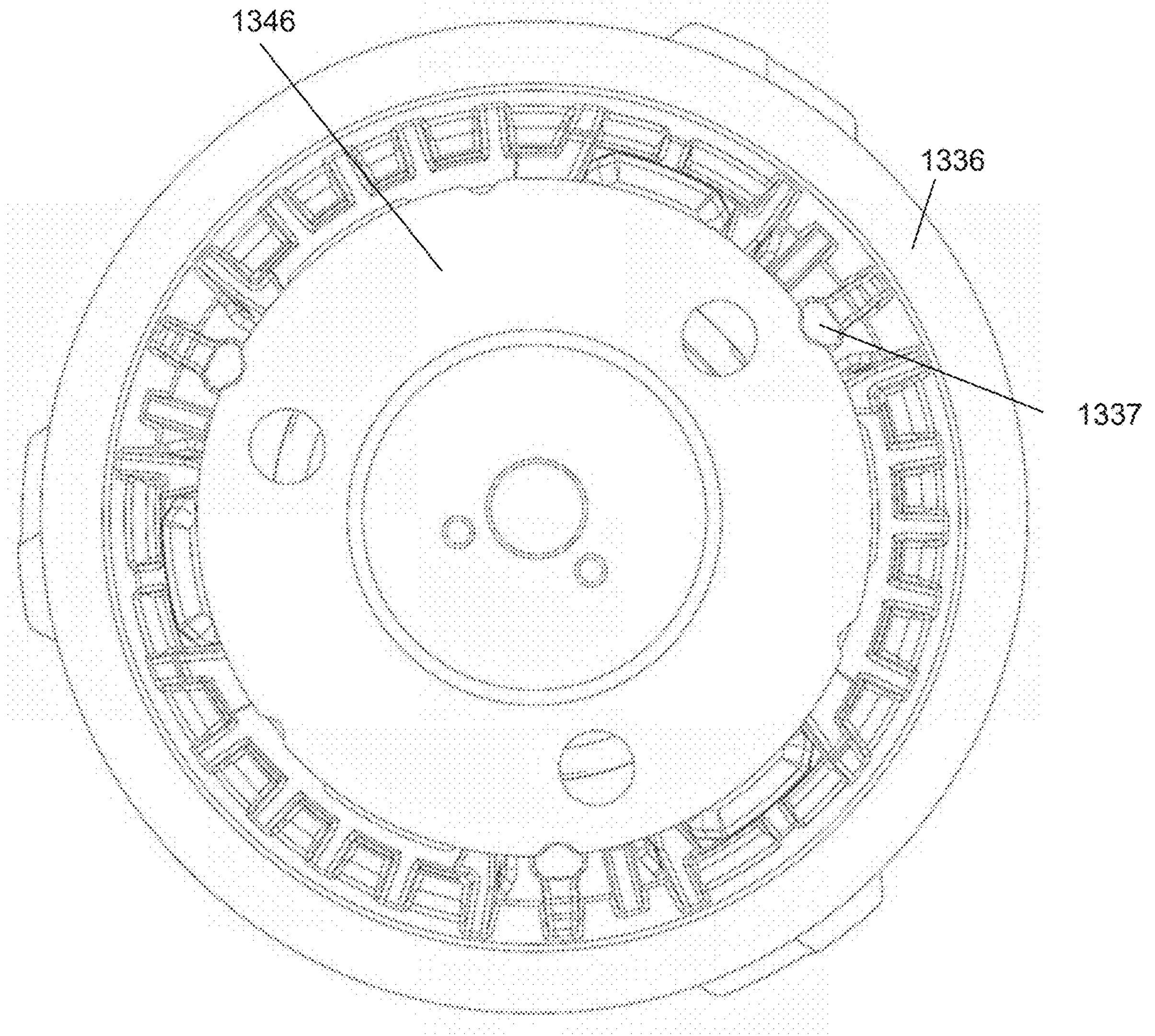
FIG. 33 depicts a cutaway view of a manifold body and a knob body of a surgical instrument of a surgical robotic system, according to embodiments.
Figure 34:
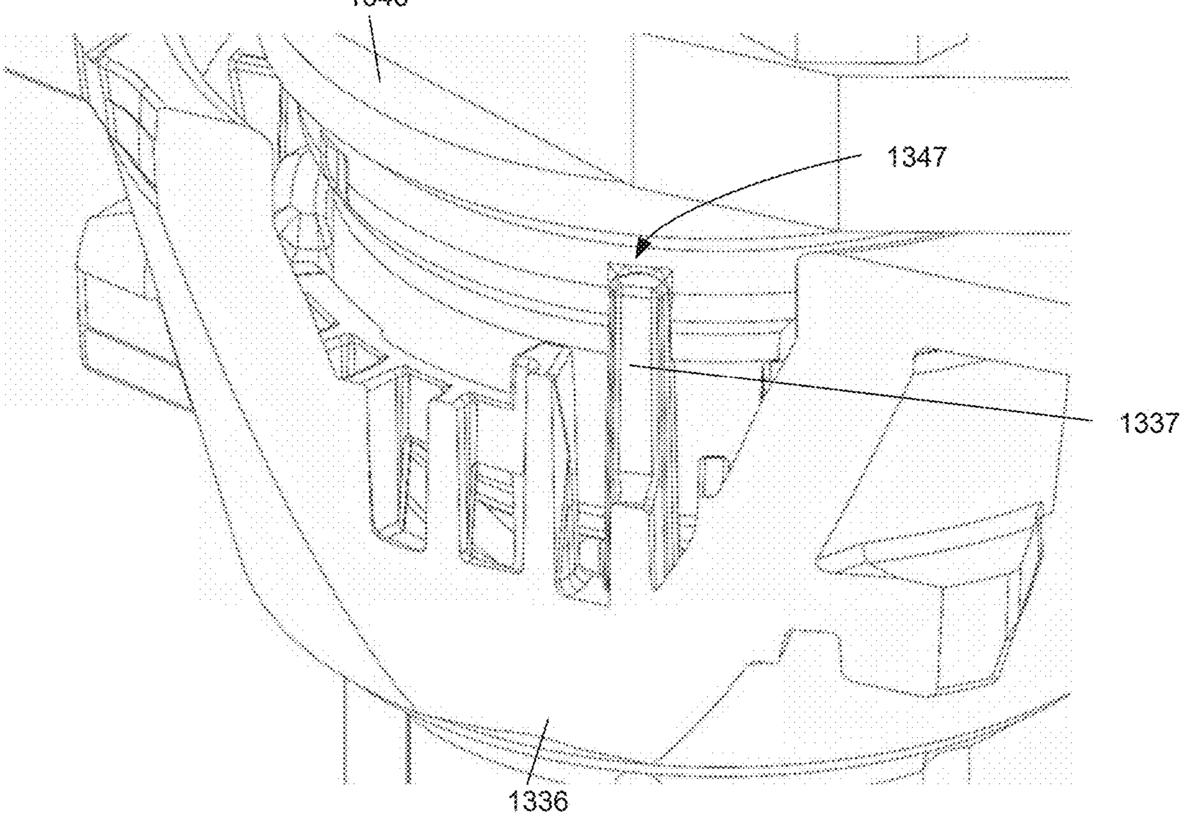
FIG. 34 depicts a close-up view of a manifold body and knob body of the surgical instrument of FIG. 33, according to embodiments.

In some embodiments, a knob body may include one or more ribs configured to click into a manifold body, which may be useful for reusable instruments. FIG. 33 depicts a rear view of a manifold body 1346 and a knob body 1336 including a click element 1337. Furthermore, FIG. 34 depicts a perspective view of the manifold body 1346 including recesses 1347 configured to receive the click element 1337 of the knob body 1336.

Figure 35:
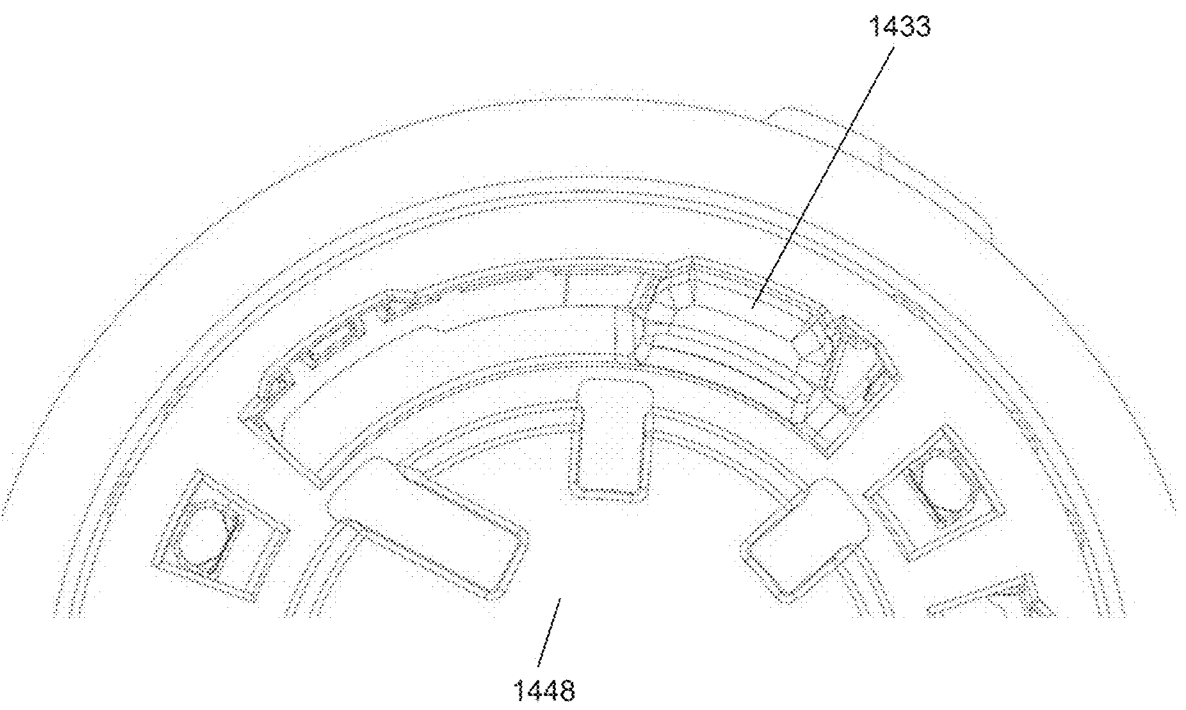
FIG. 35 depicts a detailed view of a proximal housing and a knob body of a surgical instrument of a surgical robotic system, according to embodiments.

In some embodiments, a clip of a proximal housing may be configured to click into a base cap of the instrument, which may be useful for single-use instruments. For example, FIG. 35 depicts a detailed rear view of a base cap 1448, and a click element 1433 of a proximal housing. The sealing in the instrument's base may be provided where axial or rotational movement (e.g., of the knob relative to the proximal housing, transmitted into internal components such as the manifold) compresses a sealing face against a seal (e.g., radial seal, face seal, gasket) such as with the manifold body onto the manifold seal for reusable instruments and the base cap onto the tension guide and base seal for single-use instruments.

II. Methods

Also described herein are methods of instrument coupling using axial translation and rotation. For example, a method may include inserting an instrument (e.g., any of the instruments described herein, including, for example, instruments 600, 700, 800, etc.) in a first configuration into an instrument interface of a surgical robotic system such that a proximal housing (e.g., a proximal housing 732, 832) of the instrument is disposed within the instrument interface. The instrument in the first configuration may have a knob (e.g., including knob bodies and knob caps as described herein) that is rotationally locked relative to the proximal housing. The knob of the instrument may be pushed relative to the proximal housing to transition the instrument into a second configuration in which the knob is unlocked and can rotate relative to the proximal housing. The knob can be rotated relative to the proximal housing, while the instrument is in the second configuration, to lock the instrument to the instrument interface and to couple a plurality of engagement elements (e.g., engagement elements 740, 840) of the instrument to one or more actuators of the surgical robotic system such that the one or more actuators can drive movement of the plurality of engagement elements to move the end effector in at least one degree-of-freedom.

In some embodiments, in response to pushing and/or rotating the knob relative to the proximal housing, an interior space and other interior regions of the instrument may be sealed. In some embodiments, sealing the interior space and other interior regions of the instrument includes moving a first sealing element (e.g., including any of the sealing elements described herein, such as, for example, manifold body 746, manifold ports 744, base cap 848) relative to a second sealing element (e.g., including any of the sealing elements described herein, such as, for example, manifold seal 748, manifold body 746, base seal 846) to form a fluid-tight seal therebetween that prevents fluids from leaving the interior space and other interior regions of the instrument.

In some embodiments, pushing and/or rotating the knob relative to the proximal housing to lock the instrument to the instrument interface may include pushing and/or rotating the knob relative to the proximal housing in a first direction (e.g., a clockwise direction). When the instrument is locked to the instrument interface, the knob may be pushed and/or rotated relative to the proximal housing in a second direction (e.g., a counterclockwise direction) opposite the first direction to unlock the instrument from the instrument interface. In some embodiments, before rotating the instrument in either direction, pushing of the knob (e.g., axial translation of the knob relative to the proximal housing) is necessary to unlock the knob for rotation relative to the proximal housing. Pushing and/or rotating the knob in the second direction may unseal the interior space and other interior regions of the instrument such that a cleaning fluid can enter the interior space and other interior regions of the instrument to clean and/or sterilize the interior space and other interior regions of the instrument. The design of the pushing and/or rotating the knob relative to the proximal housing permits the instrument to be safely locked in its reprocessing position (e.g., position in which the interior space of the instrument is unsealed to permit reprocessing), while the instrument is not coupled to the surgical robotic system.

In some embodiments, rotating the knob relative to the proximal housing to lock the instrument to the instrument interface may include rotating the knob until an audible and/or haptic feedback is generated. Similarly, rotating the knob relative to the proximal housing to unlock the instrument from the instrument interface may include rotating the knob until an audible and/or haptic feedback is generated. In some embodiments, the audible and/or haptic feedback may be generated in response to an arm disposed on one of the knob and/or the proximal housing interfacing with a corresponding structure disposed on the other of the knob or the proximal housing.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

The indefinite articles "a" and "an," as used herein in the specification and in the claims, unless clearly indicated to the contrary, should be understood to mean "at least one."

As used herein, the phrase "at least one" or "one or more," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one implementation, to at least one, optionally including more than one, A, with no B present (and optionally including elements other than B); in another implementation, to at least one, optionally including more than one, B, with no A present (and optionally including elements other than A); in yet another implementation, to at least one, optionally including more than one, A, and at least one, optionally including more than one, B (and optionally including other elements); etc.

As used herein, the term "and/or" when used to reference to a list of one or more elements includes an element selected from any one or more of the elements in the list of elements, but not necessarily including each and every element specifically listed within the list of elements and not excluding any combinations of elements in the list of elements.

As used herein, the term "unit" can refer to multiple features or a singular feature with one or more parts and/or components.

The invention claimed is:

1. An apparatus, comprising:

a shaft including a proximal end and a distal end, the shaft defining a lumen extending between the proximal end and the distal end;

an end effector disposed at the distal end of the shaft;

a proximal head disposed at the proximal end of the shaft, the proximal head including a housing defining an internal space configured to house a plurality of engagement elements and a knob body disposed around a proximal end of the housing, each engagement element of the plurality of engagement elements being coupled to the end effector via a force transmitting element disposed within the lumen, wherein the knob body is configured to be distally translated and subsequently rotated relative to the housing to lock the proximal head to an instrument interface of a surgical robotic system and to couple the plurality of engagement elements to one or more actuators configured to drive movement of the plurality of engagement elements to move the end effector in at least one degree-of-freedom.

2. The apparatus of claim 1, wherein the knob body includes one or more arms configured to interface with one of more corresponding features disposed on the housing to provide audible and/or haptic feedback to a user when the knob body is distally translated and subsequently rotated relative to the housing.

3. The apparatus of claim 1, further comprising a spring disposed within the knob body, the knob body configured to distally translate relative to the housing in response to a force being applied to the knob body that is sufficient to compress the spring.

4. The apparatus of claim 1, further comprising:

a first manifold structure defining one or more ports; and a second manifold structure defining one or more channels, wherein the first manifold structure is configured to rotate between a first position and a second position relative to the second manifold structure, wherein, when the first manifold structure is in the first position, the one or more ports and the one or more channels are aligned and configured to allow passage of a cleaning fluid into the interior space and other interior regions of the apparatus to facilitate cleaning and/or sterilization of internal components of the apparatus, wherein, when the first manifold structure is in the second position, the one or more ports and the one or more channels are misaligned with each other and configured to seal the interior space and other interior regions of the apparatus to prevent fluids from leaving the interior space and other interior regions.

5. The apparatus of claim 4, wherein the first manifold structure is configured to rotate from the first position to the second position in response to the knob body being rotated relative to the housing to lock the proximal head to the instrument interface.

6. The apparatus of claim 4, wherein the second manifold structure includes a stopping surface configured to block the knob body from rotating beyond a predefined position to prevent separation of the knob body from the housing.

7. The apparatus of claim 1, further comprising:

a seal including a proximally facing surface; and a base structure including a distally facing surface, the base structure configured to be axially translated toward the seal such that the seal and the base structure form a fluid-tight seal that is configured to prevent fluids from leaving an interior space and other interior regions of the apparatus, in response to the knob body being distally translated relative to the housing.

8. The apparatus of claim 7, wherein the seal is configured to deform against the distally facing surface of the base structure to form the fluid-tight seal.

9. The apparatus of claim 7, wherein the seal includes a stopping surface configured to block the knob body from rotating beyond a predefined position to prevent separation of the knob body from the housing.

10. The apparatus of claim 1, wherein the housing is a proximal housing, and the apparatus further comprises:

a distal housing; and a sealing unit disposed between the proximal housing and the distal housing, configured to form a fluid-tight seal with the plurality of engagement elements to prevent fluids from leaving an interior space and other interior regions of the apparatus.

11. The apparatus of claim 10, wherein the plurality of engagement elements is configured to extend through the sealing unit.

12. The apparatus of claim 11, wherein each engagement element of the plurality of engagement elements, when the plurality of engagement elements is coupled to the one or more actuators, is further configured to be driven by an actuator of the one or more actuators to axially translate relative to the sealing unit to move the end effector.

13. The apparatus of claim 1, wherein, subsequent to locking the proximal head to the instrument interface, the knob body is configured to be axially translated relative to the housing to allow the knob body to be rotated and separated from the instrument interface.

14. An apparatus, comprising:

a shaft including a proximal end and a distal end, the shaft defining a lumen extending between the proximal end and the distal end;

an end effector disposed at the distal end of the shaft;

a proximal head disposed at the proximal end of the shaft, the proximal head including a housing and a knob body disposed proximal of the housing; and first and second sealing elements, the first sealing element being configured to move relative to the second sealing element, wherein the knob body is configured to be distally translated and/or rotated relative to the housing to move the first sealing element to a first position relative to the second sealing element to form a fluid-tight seal that prevents fluids from leaving an interior space of the apparatus, wherein the knob body is configured to be proximally translated and/or rotated relative to the housing to move the first sealing element to a second position relative to the second sealing element to provide access for fluids to enter the interior space of the apparatus.

15. The apparatus of claim 14, wherein the knob body is configured to be distally translated and subsequently rotated relative to the housing to lock the proximal head to the instrument interface.

16. The apparatus of claim 14, wherein:

the first sealing element is a first manifold structure defining one or more ports; and the second sealing element is a second manifold structure defining one or more channels, the first manifold structure being configured to rotate relative to the second manifold structure to form the fluid-tight seal.

17. The apparatus of claim 14, wherein:

the first sealing element includes a distally facing surface, and the second sealing element includes a proximally facing surface, the first sealing element configured to be axially translated toward the second sealing element to form the fluid-tight seal.

18. The apparatus of claim 14, wherein the second sealing element includes a stopping surface configured to block the knob body from rotating beyond a predefined position to prevent separation of the knob body from the housing.

19. The apparatus of claim 14, wherein the housing is a proximal housing, and the apparatus further comprises:

a distal housing; and a plurality of engagement elements, each engagement element of the plurality of engagement elements being coupled to the end effector via a force transmitting element disposed within the lumen and being configured to translate relative to the proximal housing and the distal housing to actuate the end effector in at least one degree-of-freedom.

20. The apparatus of claim 19, further comprising:

a sealing unit disposed between the proximal housing and the distal housing, the sealing unit configured to form a fluid-tight seal with the plurality of engagement elements to prevent fluids from leaving the interior space of the apparatus.

21. The apparatus of claim 20, wherein each engagement element of the plurality of engagement elements is configured to extend through the sealing unit.

22. A method, comprising:

inserting an instrument in a first configuration into an instrument interface of a surgical robotic system such that a proximal housing of the instrument is disposed within the instrument interface, the instrument in the first configuration having a knob that is rotationally locked relative to the proximal housing, the knob including a knob body disposed around a proximal end of the proximal housing;

pushing the knob of the instrument relative to the proximal housing to transition the instrument into a second configuration in which the knob is unlocked and can rotate relative to the proximal housing; and rotating, while the instrument is in the second configuration, the knob relative to the proximal housing to lock the instrument to the instrument interface and to couple a plurality of engagement elements of the instrument to one or more actuators of the surgical robotic system such that the one or more actuators can drive movement of the plurality of engagement elements to move an end effector in at least one degree-of-freedom.

23. The method of claim 22, further comprising:

sealing, in response to pushing and/or rotating the knob relative to the proximal housing, an interior space and other interior regions of the instrument.

24. The method of claim 23, wherein sealing the interior space and other interior regions of the instrument includes moving a first sealing element relative to a second sealing element to form a fluid-tight seal therebetween that prevents fluids from leaving the interior space and other interior regions of the instrument.

25. The method of claim 23, wherein pushing and/or rotating the knob relative to the proximal housing to lock the instrument to the instrument interface includes pushing and/or rotating the knob relative to the proximal housing in a first direction, the method further comprising:

pulling and/or rotating, when the instrument is locked to the instrument interface, the knob relative to the proximal housing in a second direction opposite the first direction to unlock the instrument from the instrument interface, wherein pushing and/or rotating the instrument in the knob in the second direction unseals the interior space and other interior regions of the instrument such that a cleaning fluid can enter the interior space and other interior regions of the instrument to clean and/or sterilize the interior space and other interior regions of the instrument.

26. The method of claim 22, wherein rotating the knob relative to the proximal housing to lock the instrument to the instrument interface includes rotating the knob until an audible and/or haptic feedback is generated.

27. The method of claim 26, wherein the audible and/or haptic feedback is generated in response to an arm disposed on one of the knob or the proximal housing interfacing with a corresponding structure disposed on the other of the knob or the proximal housing.

28. The method of claim 22, further comprising:

moving the first sealing element to a first position relative to the second sealing element to form a fluid-tight seal that prevents fluids from leaving an interior space of the apparatus when the instrument is in the first configuration; and moving the first sealing element to a second position relative to the second sealing element to provide access for fluids to enter the interior space of the apparatus when the instrument is in the second configuration.

* * * * *